United States Patent
Rexroth

[11] Patent Number: 5,269,794
[45] Date of Patent: Dec. 14, 1993

[54] CUTTING BLADE ASSEMBLY FOR AN ARTHROSCOPIC SURGICAL INSTRUMENT DRIVE SYSTEM

[75] Inventor: Fred Rexroth, Dunedin, Fla.

[73] Assignee: Linvatec Corporation, Largo, Fla.

[21] Appl. No.: 437,270

[22] Filed: Dec. 4, 1989

Related U.S. Application Data

[62] Division of Ser. No. 16,140, Feb. 18, 1987.

[51] Int. Cl.⁵ ............................................. A61B 17/32
[52] U.S. Cl. .................................. 606/180; 606/170; 606/167; 606/80
[58] Field of Search ........................ 606/167–172, 606/174–180, 79, 80

[56] References Cited

U.S. PATENT DOCUMENTS

| | | | |
|---|---|---|---|
| 3,749,098 | 7/1973 | De Bennetot | 600/30 |
| 3,817,237 | 6/1974 | Bolduc | 600/30 |
| 3,924,631 | 12/1975 | Mancusi, Jr. | 600/30 |
| 4,274,407 | 6/1981 | Scarlett | 604/153 |
| 4,424,030 | 1/1984 | Smiley et al. | 128/419 F |
| 4,593,681 | 6/1986 | Soni | 128/4 |
| 4,611,601 | 9/1986 | Bowman | 128/748 |
| 4,705,038 | 11/1987 | Sjostrom et al. | 604/22 |
| 4,737,214 | 4/1988 | Lewrink et al. | 604/905 |
| 4,817,607 | 4/1989 | Tatge | 128/419 R |

Primary Examiner—David M. Shay

[57] ABSTRACT

A disposable, single use cutting blade assembly for use with a handpiece having a motor for rotatably driving the cutting blade assembly includes a plastic hub mounted on a proximal end of an outer member having a configuration to be received in a bore in the handpiece in a particular orientation relative to sensors therein and having first and second annular sections at least one of which has a recess therein for receiving a coding element to be detected by the sensors, the first and second annular sections being secured together to close the recess and hold the coding element therein.

4 Claims, 11 Drawing Sheets

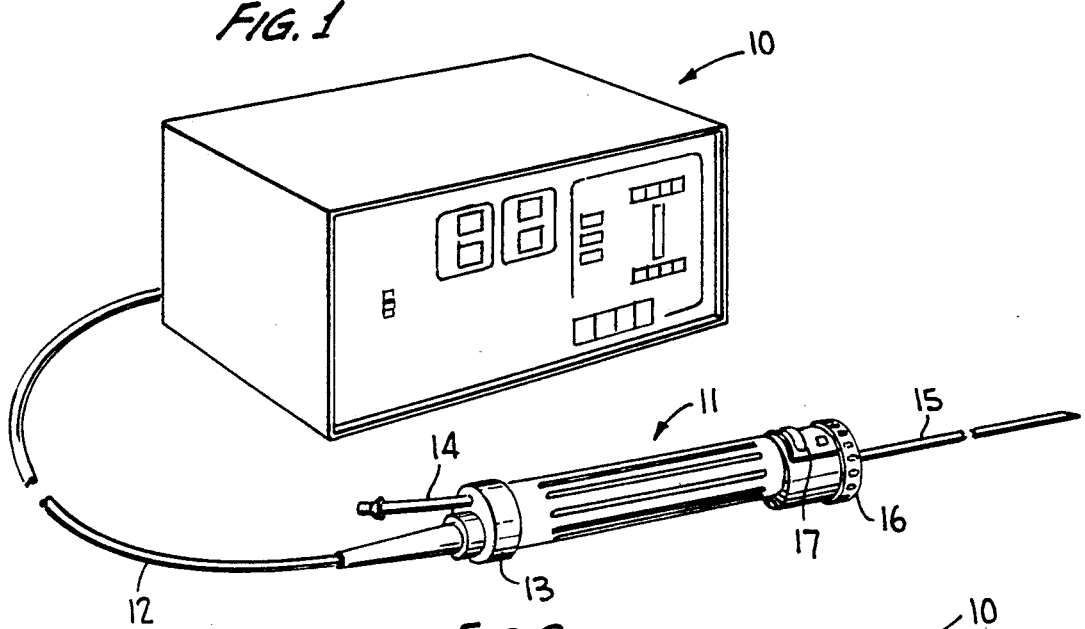
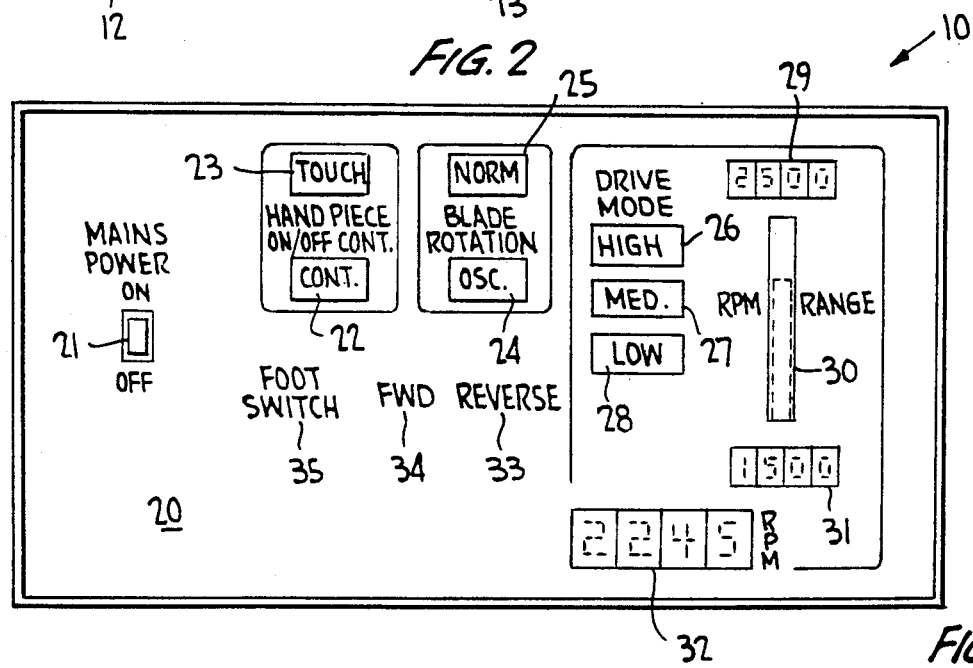
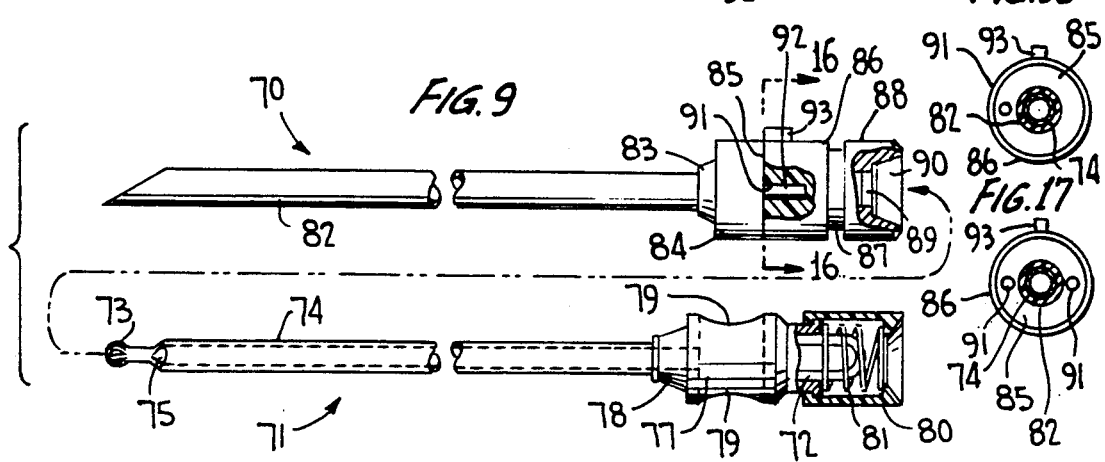

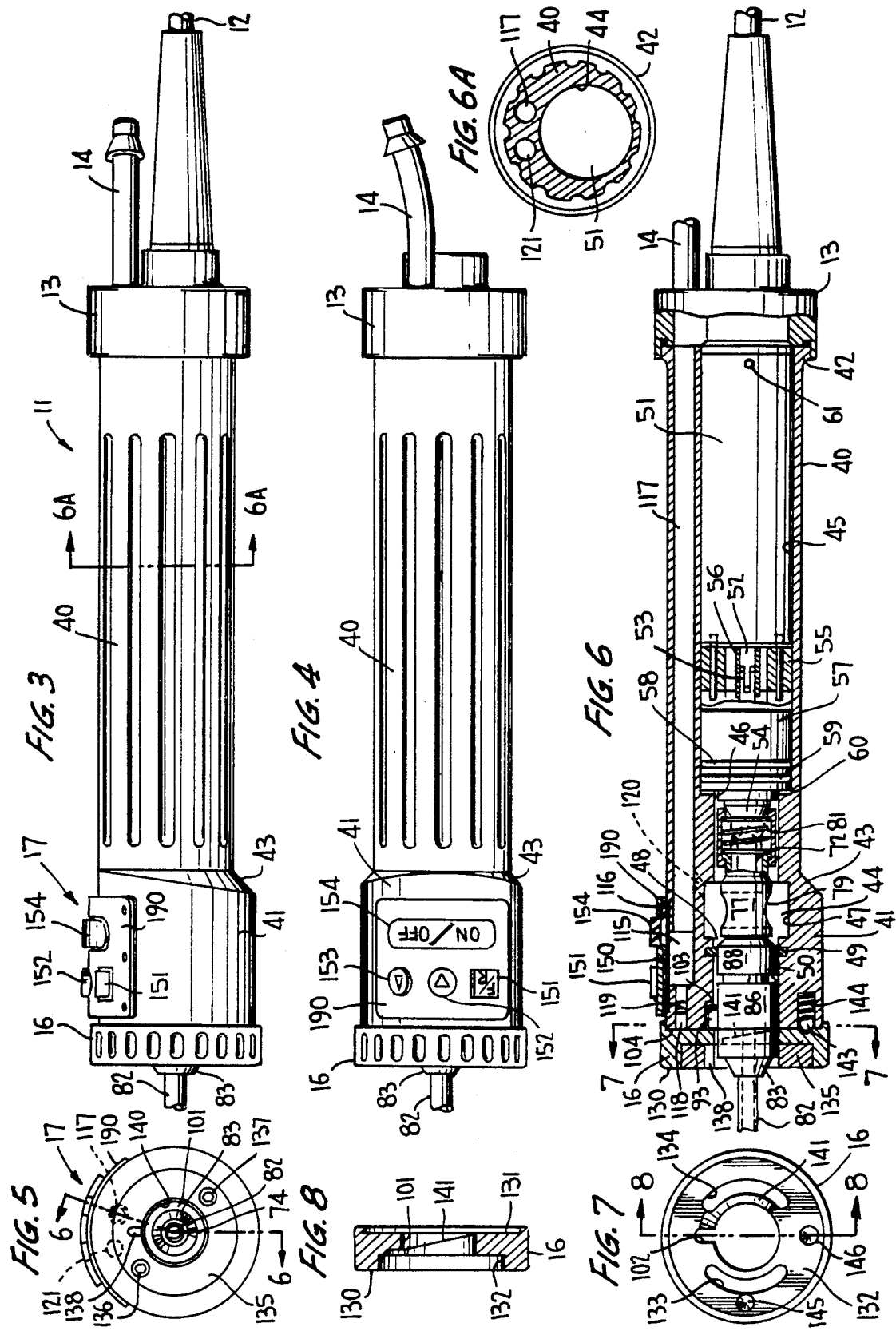

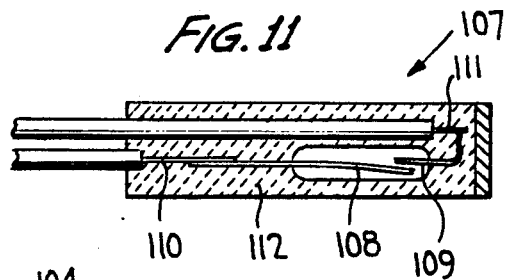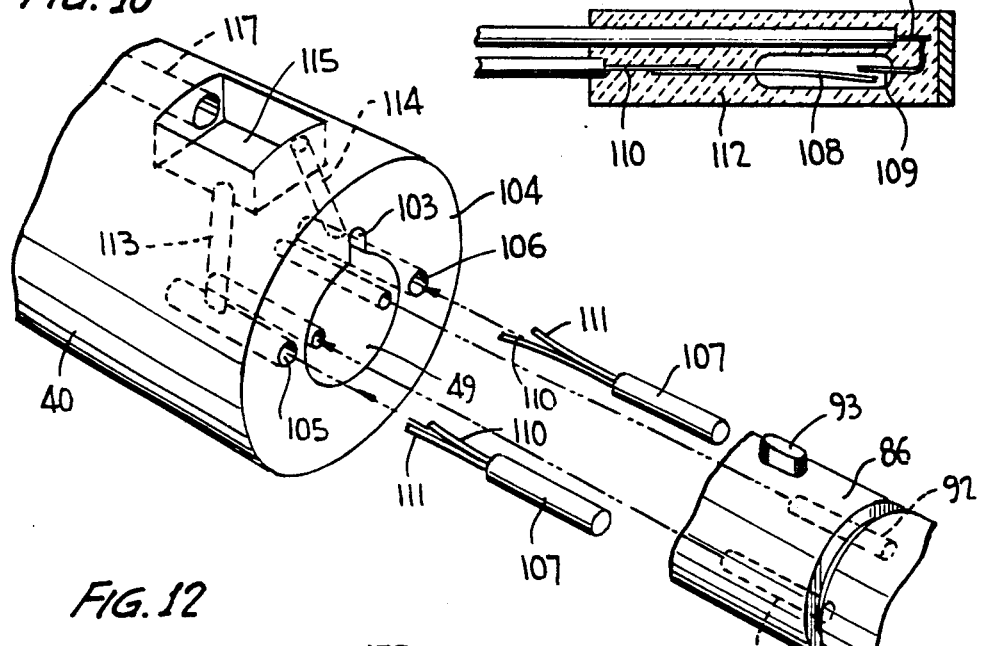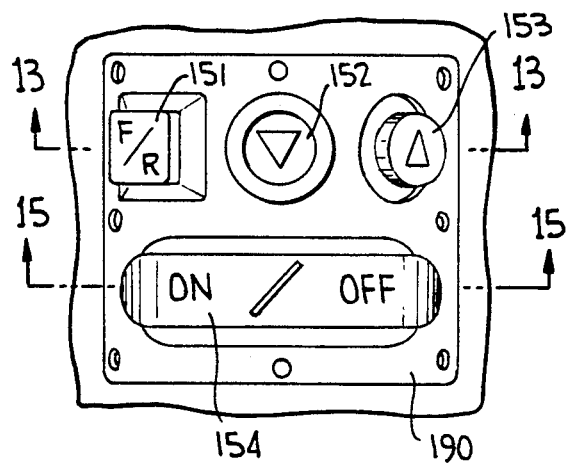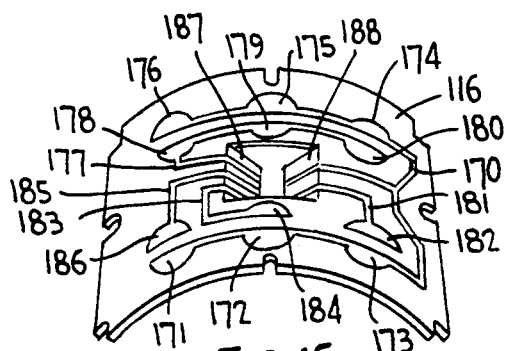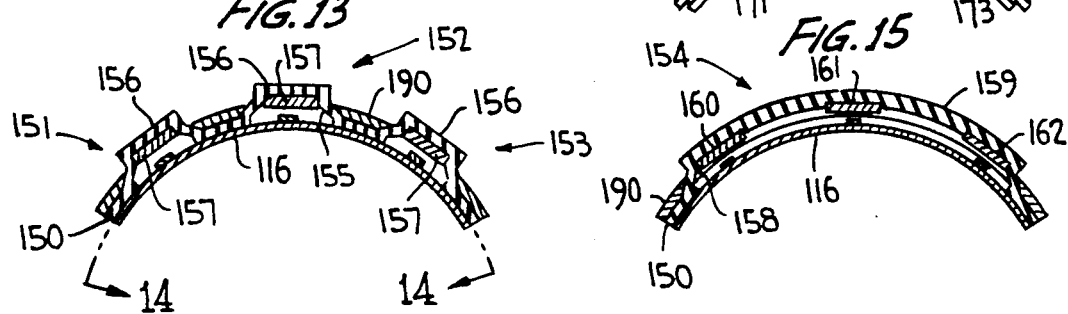

CUTTING BLADE ASSEMBLY FOR AN ARTHROSCOPIC SURGICAL INSTRUMENT DRIVE SYSTEM

This application is a division of application Ser. No. 07/016,140 filed Feb. 18, 1987.

BACKGROUND OF THE INVENTION

1. Technical Field

The present invention relates to surgical instruments and, more particularly, to instruments having rotatable motor-driven arthroscopic cutting blades capable of removing fibrous tissue lying between articulate surfaces in and around joints of the body. In addition, the instrument of the present invention can be used to balance meniscal rims and to evacuate excised tissue.

2. Discussion of the Prior Art

A typical prior art arthroscopic surgical instrument is disclosed in U.S. Pat. No. 4,203,444 (Bonnell et al) and U.S. Pat. No. 4,274,414 (Johnson et al). The disclosed instruments are elongated handpieces serving as a housing for a motor which rotatably drives a cutting blade projecting longitudinally from the forward end of the handpiece. The blade is disposed in an apertured sheath or outer tube through which excised tissue material is aspirated via suction applied through the handpiece. Controls for the motor (i.e., on/off, speed control, etc.) are located at a console and connected to the motor via a cable interconnecting the console with the handpiece.

Surgical instruments of the type described must be fabricated of material capable of withstanding autoclave temperatures (i.e., in excess of 270 degrees Fahrenheit) so that the instrument may be sterilized between surgical procedures. It is recognized in the prior art that cutting blades may be designed to be disposable (i.e., the blades are used for a single procedure and then discarded) so as to avoid the requirement of blade sterilization between procedures. However, the handpiece and the components housed therein must be repeatedly sterilized. On the other hand, the control console, which houses electrical circuitry and controls, is not required to be sterilized between uses. As a consequence, a surgeon cannot operate the console controls during a surgical procedure and must rely on an assistant to do so.

It is also recognized in the prior art that certain cutting blades, designed for specific types of surgical procedures, operate optimally within specified ranges of rotational speed. In some commercially-available systems a switch is provided on the control console to permit the operator to select a speed range that is consistent with the cutting blade to be used. A further control at the console permits the operator to select the desired speed within the selected range. A more recent development (made commercially available by Dynoics, Inc., of Andover, Mass. as the "Advanced Arthroscopic Surgical System") automatically sets the speed range appropriate for the selected cutting blade. This is achieved by providing three different cutting blade adapters (i.e., one adapter for each of the possible speed ranges) by which the cutting blade may be operably engaged with the handpiece. The adapters are coded for the desired speed range by means of one or more magnets at specific locations in the adapters. Reed switches in the handpiece are actuated by respective magnets and transmit the speed range control code information to the console to establish the correct speed range. A manual control at the console permits selection of particular speeds within the established range.

As noted above, prior art instruments of the type described have controls at the console which cannot be operated by the surgeon during a procedure without comprising sterilization. It is desirable, therefore, to provide all of the controls on the handpiece. However, there are a number of obstacles which have precluded placing the controls on the handpiece. Specifically, the entire handpiece must be capable of withstanding the temperatures experienced in an autoclave during sterilization. In addition, the controls should not increase the bulk of the handpiece, particularly in its transverse dimension, since increased bulk renders the handpiece unwieldy to manipulate during surgical procedures. Finally, the controls must be located in a convenient manner so as to permit the surgeon to quickly and easily operate each control, preferably with the one hand that holds the handpiece. Prior to the present invention, the prior art has been unable to overcome this combination of obstacles.

In addition, although it is desirable to provide for automatic setting of speed ranges to optimize specific blade operation, the prior art approach has certain disadvantages. In particular, the coded adapter is an additional part of the system which must be capable of withstanding autoclaving temperatures. Consequently, the adapter is relatively heavy and adds significantly to the overall weight of the handpiece. This adversely affects manipulability of the handpiece during surgical procedures. It is desirable, therefore, to provide for automatic speed range selection while eliminating the extra adapter part.

OBJECTS AND SUMMARY OF THE INVENTION

It is therefore an object of the present invention to provide a surgical instrument of the type described wherein controls are provided at the handpiece to permit the entire operation of the instrument to be controlled from the handpiece without adding significant weight or volume to the handpiece.

It is another object of the present invention to provide a surgical instrument of the type described which includes automatic speed range selection without requiring a separate adapter part for connecting the cutting blade to the handpiece.

A further object of the invention is to provide a disposable cutting blade for a surgical instrument of the type described, which blade can be used with both the handpiece of the present invention and with the above-described prior art instruments having speed range adapters for connecting the blade to the handpiece.

It is yet another object of the present invention to provide a switch cluster on a handpiece of the an arthroscopic surgical instrument wherein the cluster does not project transversely significantly beyond the contour of the handpiece, wherein the individual switches in the cluster are oriented to be easily accessed by the surgeon's hand in which the handpiece is held, and wherein the switch cluster and associated circuit in the handpiece are capable of withstanding autoclave temperatures.

A still further object of the present invention is to provide a surgical instrument of the type described wherein automatic setting of the optimal speed range for each disposable cutting blade is achieved by coding the disposable cutting blades themselves rather than by employing a separate coded and reusable adapter part for connecting the cutting blade to the handpiece.

In accordance with the present invention an arthroscopic surgical instrument can be controlled from a switch cluster located proximate the forward end of a handpiece. The switch cluster includes a plurality of pushbutton switches and is arrayed arcuately to correspond to the curvature of the handpiece periphery. An arcuate printed circuit board is disposed within the handpiece and closely spaced from the switch cluster so that actuation of each switch bridges a corresponding pair of printed circuit contacts. Both the arcuate switch cluster and the arcuate printed circuit board are constructed to withstand autoclave temperature to which the entire handpiece assembly is subjected when sterilized. Importantly, the small radius of curvature required for the printed circuit board renders the choice of material of paramount importance in order to prevent the board from becoming brittle when exposed to autoclaving temperatures.

The switch cluster includes four pushbuttons for: (1) controlling motor direction; (2) increasing motor speed; (3) decreasing motor speed; and (4) actuating and deactuating the motor (i.e., on/off). In the optimum arrangement, switches (1), (2) and (3) are disposed proximate the forward end of the handpiece and are aligned along an arcuate path extending along the handpiece circumference. The on/off switch (4) is disposed immediately longitudinally behind the other three switches and is elongated arcuately. The surgeon can actuate each of the switches using a single finger of the hand in which the handpiece is supported. The arcuately elongated on/off switch permits the motor to be rapidly deactuated with minimal movement of the surgeon's actuation finger.

In order to automatically select the optimal motor speed range for each cutting blade, mutually interactive coding and decoding elements are disposed directly in the cutting blade and the handpiece, respectively. In the preferred embodiment, magnets are disposed in the cutting blade and reed switches are disposed in the handpiece to effect automatic speed range control in a manner similar to the prior art described above; however, and importantly, control is effected without the need for an extra adapter part. An advantage of the magnet and reed switch arrangement is that it permits the cutting blades to be usable with the handpiece of the present invention while also mechanically fitting into the adapter of the prior art handpiece. However, other cutting blade-handpiece coding arrangements may be employed, such as: mechanical projections on the cutting blade hubs positioned to arcuate respective pressure-sealed switches in the handpiece; projections on the blade hubs blocking respective light paths in light-actuated circuits in the handpiece; etc. Whichever coding arrangement is used, the sensing components in the handpiece must be sealed so as not to be damaged during autoclaving.

BRIEF DESCRIPTION OF THE DRAWINGS

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein:

FIG. 1 is a view in perspective of a control console and handpiece unit of a preferred embodiment of the present invention;

FIG. 2 is a view in elevation of the front panel of the control console of FIG. 1;

FIG. 3 is a side view in elevation of the handpiece unit of FIG. 1;

FIG. 4 is a top view in plan of the handpiece unit of FIG. 3;

FIG. 5 is an end view in elevation of the handpiece unit of FIG. 3;

FIG. 6 is a view in longitudinal section taken along lines 6—6 of FIG. 5;

FIG. 6A is a view in transverse section taken along lines 6A—6A of FIG. 3;

FIG. 7 is a view of the rearward-facing surface of the locking ring secured to the handpiece unit as viewed along lines 7—7 of FIG. 6;

FIG. 8 is a view in section of the locking ring taken along lines 8—8 of FIG. 7;

FIG. 9 is an exploded side view in elevation and partial section of a cutting blade assembly employed in conjunction with the handpiece unit of FIG. 6;

FIG. 10 is a diagrammatic illustration of the manner in which the speed range coding of a cutting blade is detected by the handpiece unit in accordance with the principles of the present invention;

FIG. 11 is a view in longitudinal section of a reed switch employed in the handpiece unit to detect magnetic speed range coding present in cutting blade assemblies inserted into the handpiece;

FIG. 12 is a top view in plan of the control switch cluster provided on the handpiece unit of the present invention;

FIG. 13 is a view in transverse section taken along lines 13—13 of FIG. 12 and showing three of the control switches provided as part of the control switch cluster;

FIG. 14 is a view in perspective of the printed circuit board employed as part of the switch cluster assembly in the handpiece;

FIG. 15 is a view in transverse section taken along lines 15—15 of FIG. 12 and showing a fourth switch provided as part of the handpiece switch cluster;

FIG. 16 is a view in section of the cutting blade assembly taken along lines 16—16 of FIG. 9;

FIG. 17 is a view similar to that of FIG. 16 for a different cutting blade assembly coded to have a different optimal operating speed than the cutting blade assembly illustrated in FIG. 16;

DESCRIPTION OF THE PREFERRED EMBODIMENT

Figure 18A:
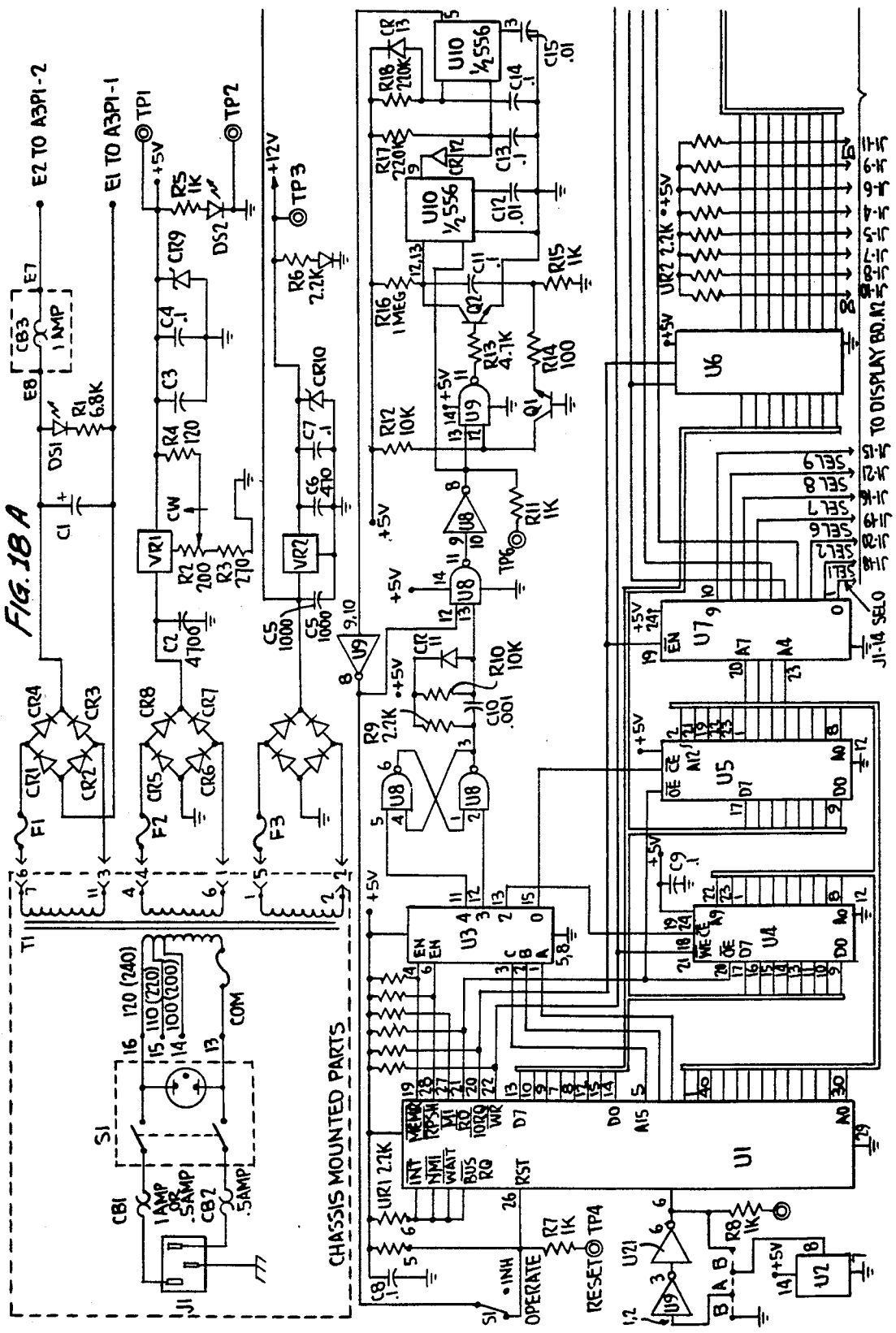
FIG. 18A and 18B are a detailed schematic diagram of the electronic components employed on the control board located in the control console.

Referring specifically to FIG. 1 of the accompanying drawings, a surgical instrument constructed according to the present invention includes a control console 10 electrically interconnected to a surgical handpiece 11 via a flexible drive unit cable 12. Cable 12 terminates at one end in a plural-conductor connector (not shown) that is received in a receptacle (not shown) secured at the rear or side of console 10. The other end of cable 12 terminates in an end cap 13 located at the proximal or rearward end of the handpiece 11. Also extending from the handpiece end cap 13 is a suction tube 14 that communicates with the handpiece interior and serves, in a conventional manner, to conduct fluid from the handpiece to a vacuum source (not shown). Typically, a control valve is disposed in the suction line intermediate tube 14 and the vacuum source to provide control over the aspiration of fluid from the surgical site and through the handpiece interior. A cutting blade 15 projects from a locking ring 16 disposed at the forward or distal end of the handpiece 11. The handpiece is generally cylindrical and the cutting blade is oriented to project substantially coaxially along the central longitudinal axis of the locking ring 16. A cluster 17 of control switches is disposed in an arcuate array proximate the forward end of the handpiece 11, the cluster being curved to correspond to the circumferential profile of the handpiece.

As illustrated in greater detail in FIG. 2, control console 10 has a front panel 20 with a number of controls and indicators. Specifically, a mains power switch 21 of the rocker type permits application and removal of primary power to and from the system. Lighted switches 22 and 23 actuate the blade drive motor in the handpiece 11. If the continuous switch 22 is pressed and released, the drive motor rotates and the switch lights; if the switch is pressed and released again, the motor stops and the switch light is turned off. If the touch switch 23 is held depressed, the motor rotates and the switch lights; release of the switch stops the motor and turns off the switch light.

The blade rotation switches 24 and 25 control the rotation direction of the motor. When the OSC switch 24 is pressed and released, the motor changes rotation directions at pre-set intervals and the switch is lighted; the NORM switch 25 is unlighted. When the NORM switch 25 is pressed and released, the motor rotates in the direction selected at switch cluster 17 in the handpiece (as described below) and the switch is lighted; the OSC switch 26 remains unlighted.

The drive mode indicators 26, 27 and 28 are lighted to indicate when a respective motor speed range has been automatically established by the particular cutting blade 15 inserted into the handpiece (in the manner described below). The high indicator 26 lights when a high speed burr blade is inserted into the handpiece. The medium indicator 27 lights when a medium speed blade is inserted into the handpiece. The low indicator 26 lights when no blade or a low speed blade is inserted into the handpiece. In the preferred embodiment disclosed herein, the high speed range extends between 1500 and 2500 rpm; the medium range extends between 500 and 900 rpm; and the low speed range extends between 75 and 400 rpm. Indicators 26, 27 and 28 are preferably bordered in different colors corresponding to the color of the blade resulting in the automatic selection of the indicated range.

The maximum speed display 29 is a four-digit light-emitting diode (LED) display for the upper limit of the speed range currently in force. The minimum speed display 31 is a four-digit LED display for the lower limit of the speed range currently in force. The RPM range LED bar display 30 indicates the relative motor speed between the displayed minimum and maximum limits and is in the form of a lighted bar having a vertical dimension which increases with increasing motor speed. The maximum and minimum displays 29 and 31 are vertically spaced, and the range display 30 is disposed therebetween to present the range indication in a position permitting an observer to easily estimate, from the bar display, the location of the actual speed within the selected operating range. An RPM digital display 32 is a four-digit LED display of the actual motor speed. It must be noted that the word "actual" employed above to describe the speed display on bar display 30 and by digital display 32 is a misnomer. The information from which these displays are derived is the control input information originating at the console 10 and applied, by electrical signal, to the motor in the handpiece 11. In other words, the display does not reflect the measured rotational speed of the motor. However, the response of the motor to the control signal is known with sufficient accuracy to permit the control information to serve as the source of the motor speed display within the precision requirements of the system.

Indicators 33, 34 and 35 are individually illuminated status indicators. The reverse indicator 33 is illuminated when the reverse motor direction is selected at switch cluster 17 at handpiece 11; this indicator flashes on and off when the motor is rotating in reverse direction. The forward indicator 34 is illuminated when the forward motor direction is selected at switch cluster 17; this indicator also flashes when the motor is rotating in the forward direction. The footswitch indicator is illuminated when a separate foot-controlled switch (not shown) is connected to console 10. When the footswitch is so connected, the on/off, forward and reverse control switches at switch cluster 17 at the handpiece are inhibited.

Handpiece 11 is illustrated in detail in FIGS. 3-8 to which specific reference is now made. Handpiece unit 11 includes an integrally formed lightweight metal body member 40 of generally cylindrical configuration. Body member 40 is sealed at its rearward end by end cap 13 and at its forward end by locking ring 16. A slightly radially enlarged flange 42 terminates the rearward end of body member 40 as best illustrated in FIGS. 6 and 6a. The forward portion 41 of body member 40 occupies approximately twenty percent of the length of that member and is cylindrical with a somewhat larger outer-diameter than the remainder of the length of body member 40. Typically, for a body member 40 having a length of 6.57 inches, the outer diameter of forward section 41 would be 1⅜ inches, while the outer diameter of the remainder of the body member 40 would be 1.2 inches. However, forward section 41 is not disposed coaxially with respect to the remainder of body member 40. In this regard, it is helpful to consider body member 40 as having a top side and a bottom side. The top side (which is seen in plan in FIG. 4 and appears as extending along the top of the body member in FIGS. 3 and 6), it is considered to be angularly centered on the line which divides switch cluster 17 into two equal transverse halves and extends longitudinally along the outside of member 40. The bottom side of body member 40 is located diametrically opposed to the top side. As best illustrated in FIGS. 3 and 6, the top side of forward section 41 is longitudinally continuous (i.e., forming a straight line) with the top side of the remainder of body member 40. At all other angular positions about the body member, forward section 41 is transversely larger than the rest of the body member 40. The transverse dimensional difference between forward section 41 and the rest of body member 40 increases with angular displacement from the top side of the body member to a maximum difference occurring at the bottom side of the member. The transition between forward section 41 and the rest of body member 40 takes the form of a chamfered surface 43 subtending an angle of approximately 45° with the longitudinal dimension of body member 40. The overall effect of the enlarged forward section 41 is a barrelled-out portion of the body member at its forward end.

As best illustrated in FIG. 6, a longitudinally-extending cylindrical bore 44, having a series of sections of different diameter, is defined entirely through body member 40. Bore 44 is concentrically disposed within forward section 41 but is displaced closer to the bottom of the remainder of body member 40. A rearward section 45 of bore 44 serves to house the drive motor for the unit and, in the described embodiment, is typically 4.475 inches long and has a diameter of 0.805 inches. Immediately forward of bore section 45 is a shorter section 46 of smaller diameter in which the motor drive shaft engages the cutting blade. Bore section 46, in the disclosed embodiment, is typically 0.805 inches long with a diameter of 0.565 inches. The next forward bore section 47 serves as an aspirator communication compartment and, in the disclosed embodiment, is typically 0.500 inches long and 0.750 inches in diameter. A short section 48 (i.e., typically 0.060 inches long, 0.565 inches in diameter) separates the aspiration communication chamber 47 from a housing section for an O-ring 49. The O-ring housing section is typically 0.110 inches long and 0.750 inches in diameter. Finally, the forwardmost bore section 50 serves to receive the hub of the cutting blade. Bore section 50 is typically 0.620 inches long and 0.565 inches in diameter. The transitions between all bore sections are annular shoulders.

The motor assembly includes a cylindrical motor 51 disposed in bore section 45 and from which a rotatably driven pin 52 projects longitudinally in a forward direction into a hollow cylindrical spacer 55. Spacer 55 remains stationary and has a hollow cylindrical drive tube 56 disposed concentrically therein. Drive tube 56 is welded, tightly fit, or otherwise secured about driven pin 52 in radially spaced relation to spacer 55. Driven pin 52 has a generally rectangular transverse cross-section and is engaged in a bifurcated rearward end 53 of a drive shaft 54 which is also received in and secured to drive tube 56. Thus, when the motor is actuated, driven pin 52 is rotated and rotatably drives the drive tube 56 and drive shaft 54. A stationary bearing housing 57 is disposed immediately forward of spacer 55 to provide a bearing support for the rotatable drive shaft extending therethrough. A plurality of O-rings 58, 59 are disposed about bearing housing 57 and serve as pressure seals in a longitudinal direction in bore section 45. Additional pressure sealing is provided by a gasket 60 disposed adjacent the annular shoulder demarcating the transition between bore sections 45 and 46 and adjacent which the forward-facing end of bearing housing 57 is forcefully urged. In this regard, the housing for motor 51 is provided with a pair of diametrically opposed apertures 61 proximate the rearward end of the motor so that pins (not shown) can be inserted transversely through suitably provided openings in the handpiece body member 40 to lock the motor assembly in place against gasket 60.

The forward end of drive shaft 54 projects into bore section 46 wherein it receives a drive tang 72, projecting from the rearward end of the cutting blade, in rotatably drivable engagement. The cutting blade assembly is illustrated in greater detail in FIGS. 9, 16 and 17 to which specific reference is now made. The cutting blade assembly includes an outer member 70 and an inner member 71. The inner member includes a tube 74 with a distal cutting end 73 which, in the illustrated embodiment, is an arthroplasty burr, although other blade types (such as meniscal open end, meniscal side cutter, end cutter, trimmer, meniscus cutter, synovial resector, and full radius resector) may be employed. Each cutting blade tube 74 is hollow and has an opening 75 proximate the distal end 73 to admit excised tissue aspirated from the surgical site in response to suction applied at the proximal end of the tube. The proximal end 76 of tube 74 is disposed in a molded member having a frusto-conical forward section 78, a hollow intermediate section 77 and a rearward section comprising the drive tang 72. A bore extends transversely through the intermediate section 77 which is recessed to a reduced radial dimension at the bore openings 79. The proximal end 76 of the hollow cutting blade tube 74 communicates with this bore so that aspirated material received in tube 74 can flow out of the cutting blade through bore openings 79. Drive tang 72 is received in a cup-like spring retainer member 80 that is open at both ends. Spring retainer member 80 has an annular lip projecting radially inward at its forward end and adapted to engage a radially outward projecting lip on the rearward section of the molded member from which drive tang 72 extends. The molded member, including sections 78, 77 and 72, and spring retainer 80 are preferably made of plastic so that the spring retainer can be forced into place on the molded member into a position whereby the two lips prevent mutual disengagement. A helical spring 81 is disposed inside spring retainer 80 to surround the drive tan 72 and serve to bias the rearward end of the spring retainer away from the blade. In this manner, spring 81 urges the two annular lips axially against one another in the absence of any axial force in opposition to the spring. Whereas tube 74 and burr 73 are made of metal (preferably stainless steel), the remainder of the inner member 71 is preferably made of plastic.

Outer member 70 includes a hollow metal (preferably stainless steel) tube 82 having an inside diameter which is larger than the outside diameter of tube 74 in inner member 71. The length of tube 82 is such that the distal end of tube 74, including the cutting blade 73 and opening 75, project through the open distal end of tube 82 when inner member 71 is inserted into and through inner member 70 in the manner described below. In this regard, the inner and outer members are conventional. Tube 82 extends through a hollow hub preferably made of plastic material and having a short hollow frusto-conical forward end 83 formed integrally with a cylindrical section 84 having an annular rearward-facing surface that is automatically welded or otherwise sealingly disposed against a fixed forward-facing annular surface 85 of a hollow cylindrical section 86. Immediately rearward of hollow section 86 is a hollow cylindrical section 87 of reduced outer diameter. A proximal end section 88 of the hub takes the form of a hollow cylinder with an outer diameter corresponding to that of sections 86 and 84. A central bore 89 extends longitudinally through the integrally formed molded plastic sections 86, 87 and 88 and is generally cylindrical except at its proximal end where it has a frusto-conical contour 90 to receive the frusto-conical section 78 of the inner member 71. Bore 89 is sized to permit tube 74 to extend therethrough, and through a similar aligned bore in sections 83 and 84, into tube 82. The cutting blade, when thusly assembled, has the forward-facing annular shoulder of section 77 of the inner member 71 disposed proximate the rearward-facing proximal end of rearward section 88 of outer member 70. The arrangement permits the inner member 70 to rotate within outer member 70 about the axis of tube 74.

As best illustrated in FIGS. 16 and 17, one or more cylindrical recesses 91 are defined in hub section 86 at the forward-facing surface 85. The number of such recesses 91 provided for any given cutting blade depends upon the optimal rotational speed range for that blade. Specifically, there are three possible speed ranges in the system of the preferred embodiment, although it will be apparent that any number of speed ranges may be designed into the system. For low speed blades, hub section 86 has no recesses defined in surface 85. For medium speed blades, hub section 86 has one recess 91 defined therein at a location radially spaced from the central bore 89 (as illustrated in FIG. 16). For high speed blades, hub 86 has two recesses 91 disposed symmetrically on opposite sides of the central bore 89 (as illustrated in FIGS. 17). Each recess 91 receives a magnet 92 that serves as a coding element for the blade. The material from which the hub is fabricated must be such as to permit the magnetic field of magnets 92 to be sensed in handpiece 11 when the cutting blade is inserted therein (in the manner described below). In order to assure proper orientation of magnet 92 in the handpiece, hub section 86 is formed with a locator stub 93 projecting a short distance radially outward from section 86 at a prescribed annular location on the hub circumference. Specifically, stub 93 is displaced 90° from each of the two possible angular orientations of recesses 91.

Referring again to FIGS. 3-8, locking ring 16 is provided with a central aperture 101 extending longitudinally therethrough and aligned with bore section 50 in body member 40. The diameters of aperture 101 and bore section 50 are slightly greater than the diameter of hub sections 86 and 88 and spring retainer 80. Locator stub 93 in hub sections 86, however, projects radially beyond the boundary of aperture 101 and bore section 50. In order to permit the cutting blade assembly to be accommodated into the handpiece through aperture 101, a radially-extending slot 102 is defined in locking ring 16 at the periphery of aperture 101. A corresponding radially-extending slot 103 is disposed at the periphery of bore section 50 and is sized to permit locator stub 93 to be received therein when the cutting blade assembly is inserted into the handpiece in the manner described below.

As best illustrated in FIG. 10, the forward-facing end surface 104 of body member 40 is provided with two generally cylindrically recesses 105, 106 disposed on diametrically opposite sides of bore section 50 and radially spaced from that bore section. Recesses 105 and 106 are spaced on opposite sides and 90° from slot 103, and each has a generally cylindrical read switch assembly 107 disposed therein. Reed switch assembly 107, which is illustrated in greater detail in FIG. 11, includes a pair of normally open switch contacts 108, 109 embedded in a glass capsule 12 or potting compound, along with respective lead wires 110, 111 which are insulated and extend from the rearward end of the capsule. The reed switches are oriented to sense the presence of respective magnets 93 in the blade assembly hub so as to register the coded information from the inserted blade. This information, in the form of open/closed conditions of contacts 108, 109, is transmitted to the control circuity in the console 10 via wires 110, 111. The insulated wires 110, 111 at the rear of the reed switch assembly pass into respective recesses 105, 106 and through respective obliquely oriented wire-conducting channels 113, 114. These channels terminate in a generally rectangular recessed space 115 in the top side of forward section 41, immediately below the switch cluster 17 and its associated printed circuit board 116. The rear wall of recess 115 opens to a channel 117 that runs rearwardly for the remaining length of body member 40. Channel 117 conducts reed switch wires 110, 111 and wires from printed circuit board 116 to the rearward end of body member 40 where the wires form part of cable 12 along with the wires connected to motor 51. The wires in cable 12 conduct signals to and from the circuitry in the control console.

A bore 118 extends from the forward end of surface 104 of body member 40 into recess 115. Bore 118 is used during assembly of the handpiece unit as an access opening for potting compound. Once sufficient potting compound has been delivered into the handpiece, bore 118 is sealed by a set screw 119 and additional compound.

Referring again to FIG. 6, an aspiration path for excised tissue material flowing through hollow tube 74 and out through bore openings 79 in the cutting blade is provided via widened bore section 47. Specifically, when the cutting blade assembly is properly inserted into the handpiece, section 77 of the molded part of the inner blade member 71 is disposed within bore section 44. Openings 79 are clear from the bore walls to permit aspirated material to flow into bore section 47 and through an oblique channel 120 extending both rearwardly and toward the top side of body member 40 until terminating in a suction channel 121. This suction channel extends rearwardly in parallel spaced relation to wire channel 117 until reaching the rearward end of body member 40 where it communicates, via end cap 13, with suction tube 14. As described above, the suction tube 14 communicates with a source of suction pressure (not shown) via a control valve (not shown) to permit selective aspiration from the surgical site. The O-ring 49 disposed in bore section 48 surrounds hub section 86 of the cutting blade assembly to provide a pressure seal forwardly of the aspiration chamber formed by bore section 44. Gasket 60 and O-rings 58, 59 provide pressure seals rearwardly of the aspiration chamber.

Locking ring 16 is a generally cylindrical member having an exposed forward-facing surface 130 and a rearward-facing surface 131 abutting surface 104 of body member 40. The locking ring is made of metal and includes a raised annular lip surrounding surface 131 and extending over a short length of the body member 40. A circular recess 132 in surface 130 is disposed concentrically about aperture 101. Arcuate channels 133, 134 are defined through the locking ring within recess 132. Channels 133 and 134 are equally spaced from slot 102 and are disposed symmetrically about aperture 101.

Each channel subtends approximately 90° of arc at a constant radial distance from the center of aperture 101. A disc-shaped spacer 135 is disposed in recess 132 and is provided with a central aperture 140, aligned with aperture 101, and with two screw holes spaced by 180° and aligned with corresponding tapped bores in forward end surface 104 of body member 40. Screws 136, 137 pass through the screw holes and threadedly engaged in the tapped bores to secure spacer 135 to body member 40. These screws pass through respective channels 134, 133 to permit locking ring 16 to be rotated relative to spacer 135 and body member 40. Such rotation is limited by the lengths of the channels 133, 134 (i.e., 90°). Spacer 135 also has a slot 138 defined therethrough to extend radially from central aperture 140. When slot 138 is rotatably aligned with slot 102 in locking ring 16, and with slot 103 in bore section 50, locator stub 93 on the cutting blade assembly can freely pass into and out of the body member 40.

The rearward-facing side of the locking ring 16, as seen in FIGS. 7 and 8, includes an arcuate ramp surface 141 extending approximately 140° from slot 102 along the outer edge of aperture 101 and the inner edge of arcuate slot 134. Ramp surface 141 serves as a camming surface for inserting the cutting blade into the handpiece. Specifically, in one extreme rotational position of locking ring 16, slot 102 is aligned with slot 138 in spacer 135 and with slot 103 in bore section 50. It is to be noted that slots and with slot 103 in bore section 50. It is to be noted that slots 138 and 103 are permanently aligned but that slot 102 can be misaligned as a function of the rotation of the locking ring. When all the slots are aligned, the cutting blade assembly may be inserted through the locking ring as far as possible. The open rearward end of the spring retainer member slides over the forward end of the motor drive shaft 54 (as best illustrated in FIG. 6) until the edge of the opening in member 84 abuts the frusto-conical surface of the drive shaft immediately rearward of the forward end of the drive shaft. In this position the locator stub 93 on the cutting blade hub is disposed substantially entirely in slot 103 in bore section 50 with just a small portion of the stub projecting partially into slot 102 of the locking ring. If the locking ring is then rotated 90° to its other extreme position, the camming surface 141 gradually forces stub 93, and with it the cutting blade assembly, rearwardly. This pushes the drive tang 72, in opposition to the bias force of spring 81, further rearward in spring retainer 80 and into more positive engagement with the drive shaft 54. Thus, in the installed position of the blade assembly, spring 81 is axially compressed as camming surface 141 forces locator stub fully into the slot 103 in bore section 50.

In order to remove the cutting blade assembly, the locking ring is rotated 90° in the opposite direction to its initial extreme position, thereby gradually releasing the compression force on spring 81. When slot 102 becomes aligned with slots 138 and 103, spring 81 forces the cutting blade assembly slightly forward so that a portion of stub 93 extends into slot 102. The blade assembly may then be easily removed and replaced by another blade.

The two extreme positions of the locking ring are maintained by means of a detent ball 143 and spring 144 located in a recess in forward-facing surface 104 of body member 40. The detent ball and spring cooperate with two dimples 145, 146 formed at 90° spaced locations in the rearward-facing surface of the locking ring to provide stops at the two extreme rotational positions of the locking ring. Dimples 145 and 146 are configured as spherical segments to match the configuration of ball 143. The locking ring 16 is retained in fixed axial or longitudinal position between the spacer 135 and body member 40 by means of screws 136, 137, but is free to rotate with respect to the spacer and body member by virtue of the 90° channels 133 and 134 are slide about the screws.

An important feature of the present invention is the switch cluster 17 located on the top side of body member 40 in forward section 41. Specifically, and referring to FIG. 6, a printed circuit board 116 is contoured to fit into a shallow recess in forward section 41 of body member 40. This shallow recess surrounds the deeper recess 115 so that lead wires from the printed circuit board can pass into the recess 115 and through wire conducting channel 117 to the cable assembly. The printed circuit board 116 is illustrated in greater detail in FIG. 14 and is transversely arcuate to match a segment of the circumference of forward section 41 of body member 40. Typically, the printed circuit board 116 is made from a rectangular blank or sheet of decarburized steel having a length (i.e., longitudinally of body member 40) of 0.998 inches, a width (i.e., along the circumference of forward section 41) of 1.294 inches and a thickness of 0.013 inches. The sheet is bent to be curved about its longitudinal center line with a radius of curvature of approximately 0.656 inches and so as to subtend an arc of 113°. It is to be understood that these dimensions are by way of example only are and not to be construed as limiting on the scope of the invention, except for the considerations set forth below. A layer of porcelain is deposited on each surface of the sheet, and the metal circuit elements are deposited, or otherwise formed, on the top porcelain surface. A pair of flaps 187, 188 at the center of the sheet are bent downwardly into recess 115 to provide access for lead wires running from the deposited circuitry on the top surface of the board to the handpiece cable via channel 117. The particular materials used in fabricating the printed circuit board 116 are important since the board must withstand autoclave temperatures without becoming brittle and breaking. This becomes a particularly important consideration where, as where, the printed circuit board must be curved at a relatively small radius of curvature. Typically, in order for the printed circuit board to conform to the curvature of the handpiece circumference, the radius of curvature is on the order of 0.6 to 0.7 inches, and usually is in the narrower range of 0.64 to 0.66 inches. Although the decarburized steel sheet with porcelain coatings on both sides is suitable for the printed circuit board of the present invention, I have found that other materials are also suitable. For example, the printed circuit board may be a sheet of aluminum on which a thick film process is employed to form a layer of epoxy with gold silk screening to define the circuit elements. Alternatively, the board may be a thin film TEFLON weave board with copper laminate used to form the circuit elements. Another alternative is a fiberglass epoxy substrate with copper laminate forming the circuit elements.

Referring to FIGS. 12, 13, and 15, an integral electrically non-conductive silicone rubber sheet 150, having a Durometer on the order of seventy, is disposed atop the printed circuit board 116. A plurality of resilient push button switches 151, 152, 153 and 154 are defined in sheet 150. Each of the pushbutton switches 151, 152 and 153 includes a resilient dome-like member 155 tapering from an open end facing the printed circuit board 116 to a closed end 156 remote from the printed circuit board. The closed end 156 encompasses a smaller area and has a smaller periphery than the open end. An electrically conductive member 157 is secured to the underside of the closed end 156. The electrically conductive member of each of pushbuttons 151, 152 and 153 is normally disposed in spaced alignment between a respective pair of contacts on the printed circuit board so that, when the pushbutton is depressed, those contacts are electrically bridged by the conductive member 157. Pushbutton switch 151 has a square-shaped closed end 156 and serves as the forward/reverse control switch. Pushbutton switches 152 and 153 are circular and serve as the decrease speed and increase speed control switches, respectively, for the motor. Pushbutton switches 151, 152 and 153 are disposed in transversely aligned spaced relation along the circumference of the handpiece.

Pushbutton switch 154 is the on/off control switch for the motor and is generally oval-shaped. In this regard pushbutton switch 154 is slightly rearward of the aligned switches 151–153 and has a length along the circumference of the handpiece which corresponds approximately to the total spaced length of the aligned switches 151–153. In this manner then on/off switch 154 is immediately proximate any of the other three switches and can be quickly actuated to turn the motor on or off. Pushbutton switch 154 is also formed as a dome-like member 158 with a closed small end 159 and an open larger end. Three electrically conductive members 160, 161, 162 are secured in transversely spaced relation (i.e., in the same spaced relation as pushbutton switches 151, 152 and 153) to the underside of closed end 159 and are positioned opposite three respective pairs of contacts on the printed circuit board 116. These printed circuit board contacts are connected electrically parallel to one another so that bridging of any one or more of the contact pairs effects the same on/off function. In the preferred embodiment, electrically conductive member 160 is longitudinally aligned with electrically conductive member 157 of switch 151; electrically conductive member 161 is longitudinally aligned with electrically conductive member 157 of switch 152; and electrically conductive member 162 is longitudinally aligned with electrically conductive member 157 of switch 153. The transverse spacing of conductive members 160, 161 and 162 assure that substantially any location along the transverse dimension of switch 154 can be depressed to effect actuation of the on/off function. In this regard, the transverse spacing between successive electrically conductive members 160, 161 and 162 is only slightly greater than the transverse dimension of each of these individual electrically conductive members. For the given Durometer of sheet 150, effective actuation of switch 154 may be achieved from anywhere along the transverse dimension of that switch.

The circuitry on printed circuit board 116 is illustrated in FIG. 14 to which specific reference is now made. All contact pairs for all four switches 151, 152, 153 and 154 include one contact associated with a common lead 170 serving as a circuit ground in the system control circuitry. In this regard, lead 170 surrounds the other leads on three sides and includes six contacts 171, 172, 173, 174, 175 and 176 at spaced location along its length. A second lead 177 is associated only with on/off switch 154 and includes three contacts 178, 179 and 180 along its length. Contacts 176 and 178 are closely spaced from one another and are positioned under electrically conductive member 162 to be electrically bridged by that member when it is pressed against the printed circuit board 116. In a similar manner contacts 175 and 179 are positioned to be selectively bridged by conductive member 161, and contacts 174 and 180 are positioned to be selectively bridged by electrically conductive member 160.

A third lead 181 has a single contact 182 positioned adjacent but spaced from ground contact 173 so that these two contacts can be selectively bridged by the electrically conductive member 157 of the forward-/reverse switch 151. A fourth lead 183 has a single contact 184 positioned adjacent but spaced from ground contact 172 so that these two contacts can be selectively bridged by the electrically conductive member 157 of the decrease speed switch 152. A fifty lead 185 has a single contact 186 positioned adjacent but spaced from ground contact 171 so that these two contacts can be selectively bridged by the electrically conductive member 157 of the increase speed switch 153.

All five leads 170, 177, 181, 183 and 185 extend along one or the other of the centrally located and downwardly bent flaps 187, 188 to connect to appropriate wires in recess 115. As noted above, such wires are conducted through channel 117 to the cable assembly at the rearward end of the handpiece.

A metal cover plate or bezel 190 is disposed over sheet 150 and is apertured to permit pushbuttons 151, 152, 153 and 154 to project therethrough. A plurality of screw holes disposed about the border of plate 190 are aligned with respective holes in sheet 150 and with edge notches in printed circuit board 116 in order to secure these elements together and to body member 40 via respective screws threadedly engaging respective tapped bores in the shallow body member recess in which printed circuit board 116 resides.

All of the components of the handpiece 11 are made of materials that are capable of withstanding the high temperatures to which they are exposed when the handpiece is sterilized by autoclaving or the like. A potting compound or epoxy is used to protect the electrical components from damage during autoclaving.

With brief reference to FIG. 9, the forward section 84 of the hub member for the cutting blade may be colored in a manner to match the border of one of the indicators 26, 27, 28 so as to provide a color-coded indication on the cutting blade of the speed range corresponding to the correspondingly color coded indicator border.

The body member 40 is made of lightweight material and is balanced to facilitate small joint arthroscopy. Longitudinally-extending fluting along the length of the body member facilitates handling. The body member houses a powerful brushless motor providing the necessary torque and speed for all types of powered arthroscopic procedures. The location of switch cluster 17 on the handpiece greatly facilitates operation by the surgeon. Automatic speed range is provided without the need for heavy adapters which must be sterilized after each surgical procedure. Although the motor may be completely controlled from the handpiece, a footswitch is provided to permit control over forward and reverse rotation while allowing the surgeon to select the proper speed from the handpiece. The entire handpiece and cord may be immersed and soaked in a sterilized solution without corroding. In addition, the unit may be flashed, steamed autoclaved or gas sterilized.

The use of disposable, single-use cutting blades assures factory-fresh sharpness with every surgical procedure and eliminates the expense and time delay involved in sharpening and re-sharpening blades.

Operation is controlled by a sophisticated microprocessor system. The microprocessor and related electronic circuitry, of itself, does not constitute part of the present invention; however, for purposes of fully disclosing the best mode of carrying out the invention, a microprocessor and related electronic circuitry are disclosed herein in FIGS. 18 and 23 and are briefly described in the following paragraphs. It is to be understood, however, that the microprocessor and electronic system described herein serve as only one embodiment for effecting the inventive features described above, and that other arrangements of electronic circuits and/or microprocessor units may be used to effect the inventive features. In furtherance of the requirement for disclosing the best mode of carrying out the invention, the application includes appendices containing a program listing for the microprocessor and a list of the components illustrated in the circuits of FIGS. 18-23.

Figure 18B:
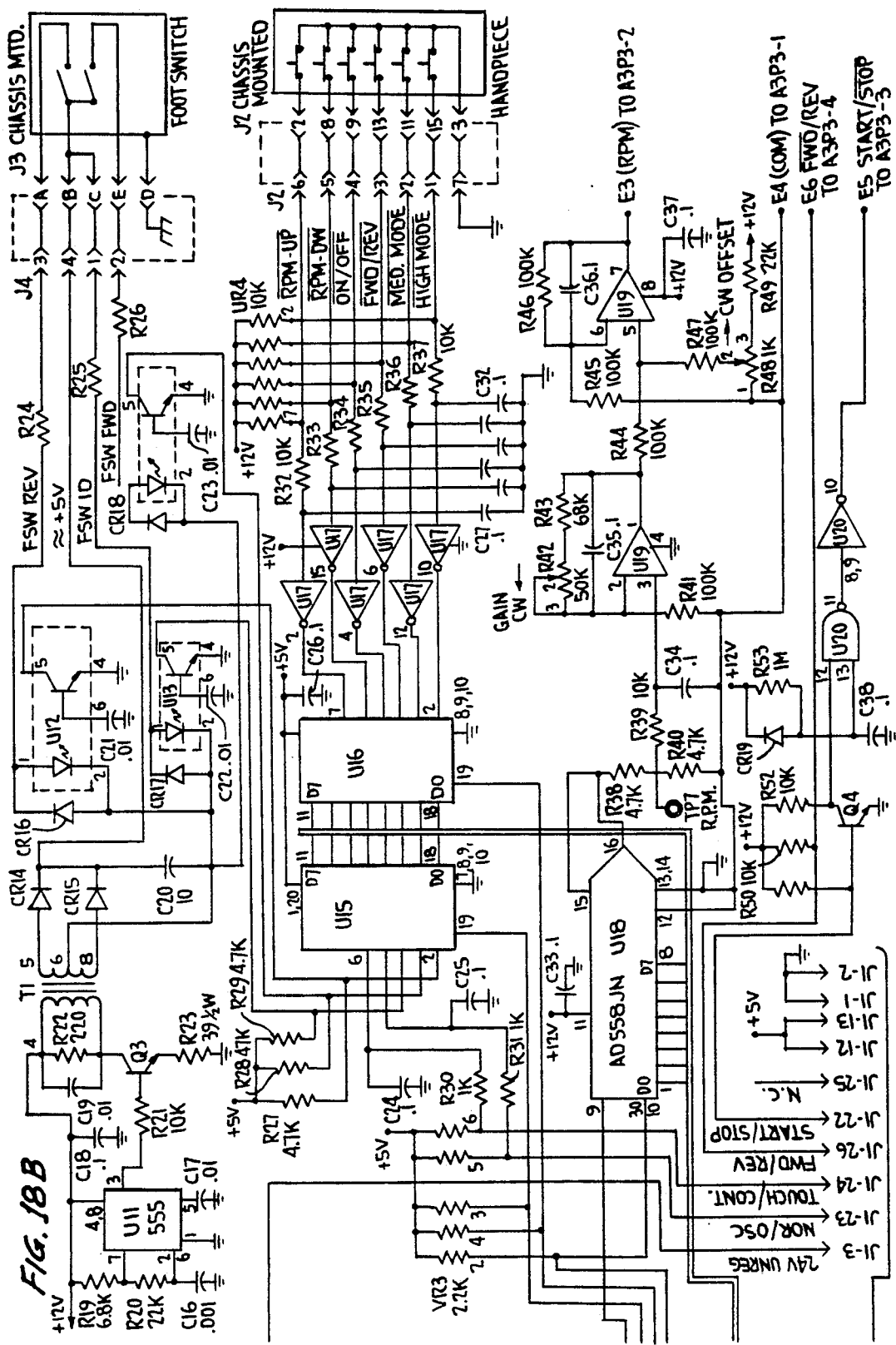
Figure 19:
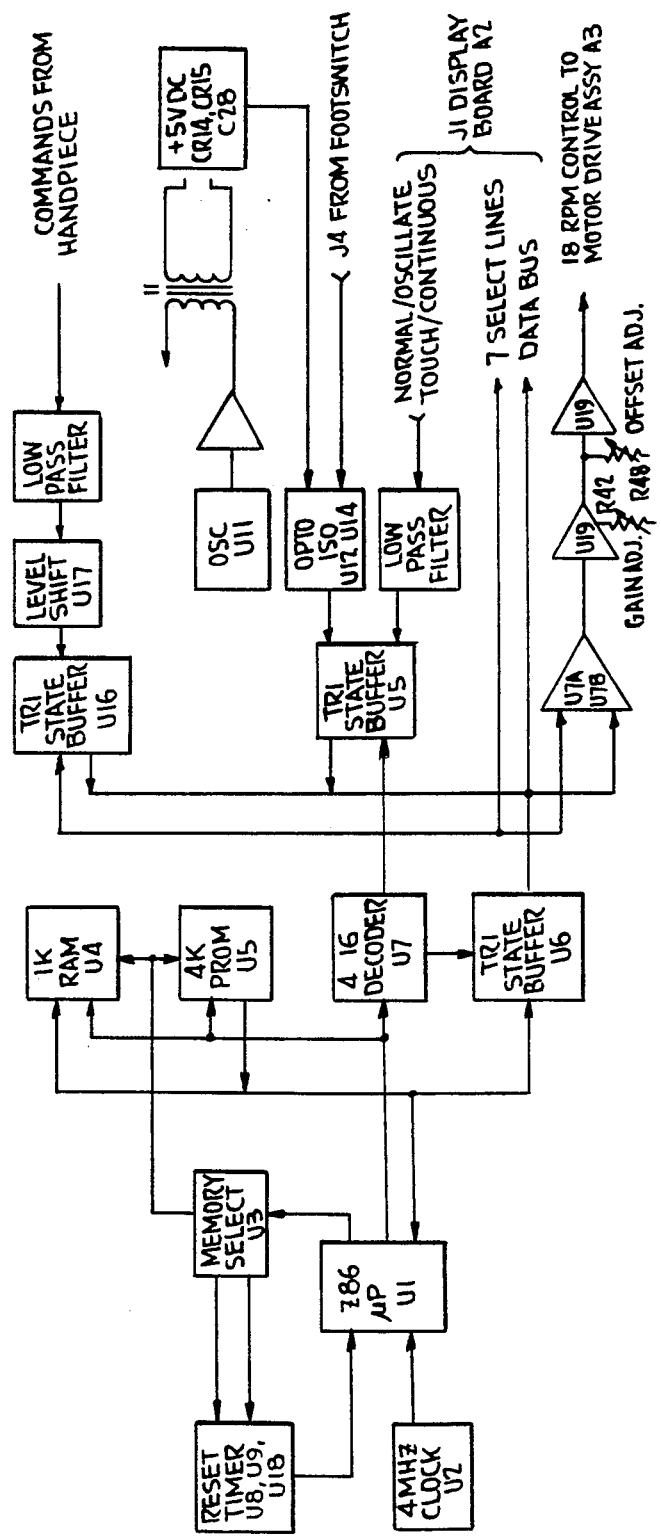
FIG. 19 is a functional block diagram of the control board.
Figure 20:
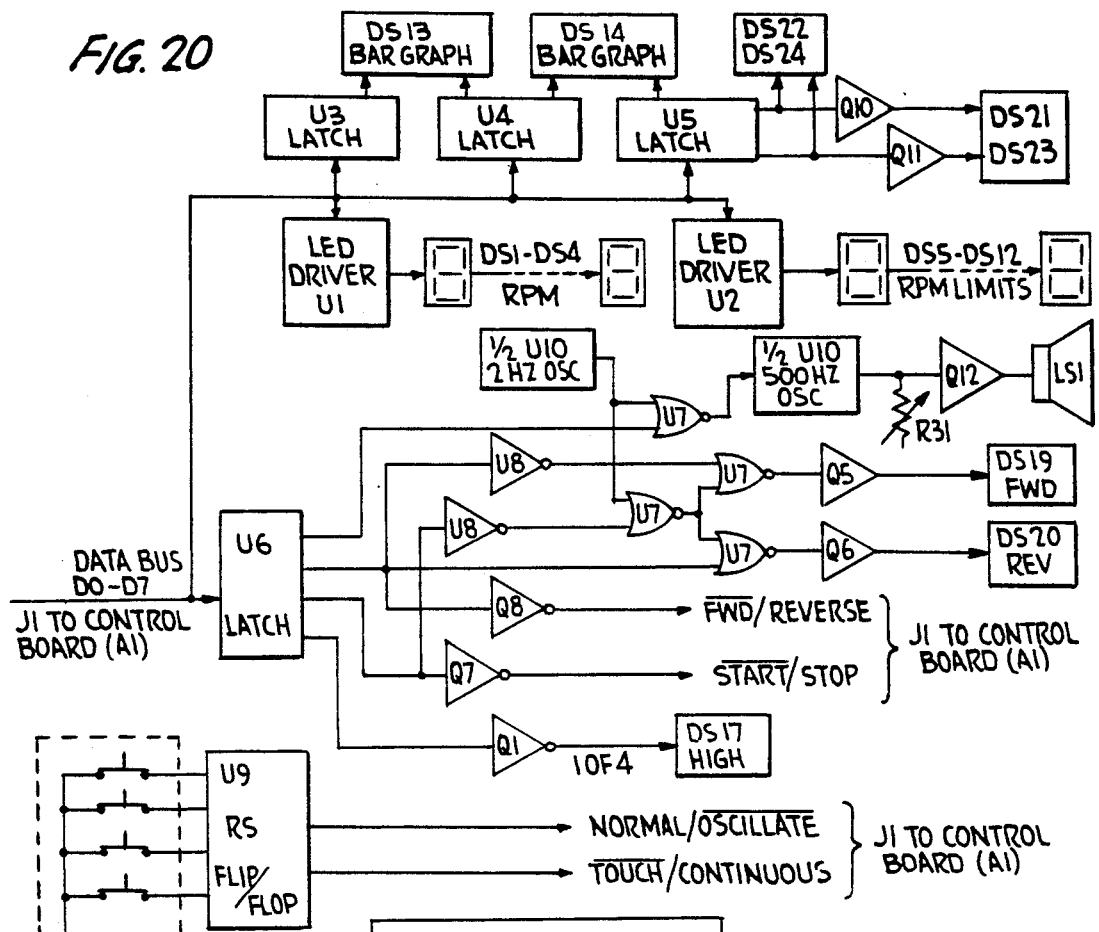
FIG. 20 is a functional block diagram of the display board located in the control console.
Figure 22:
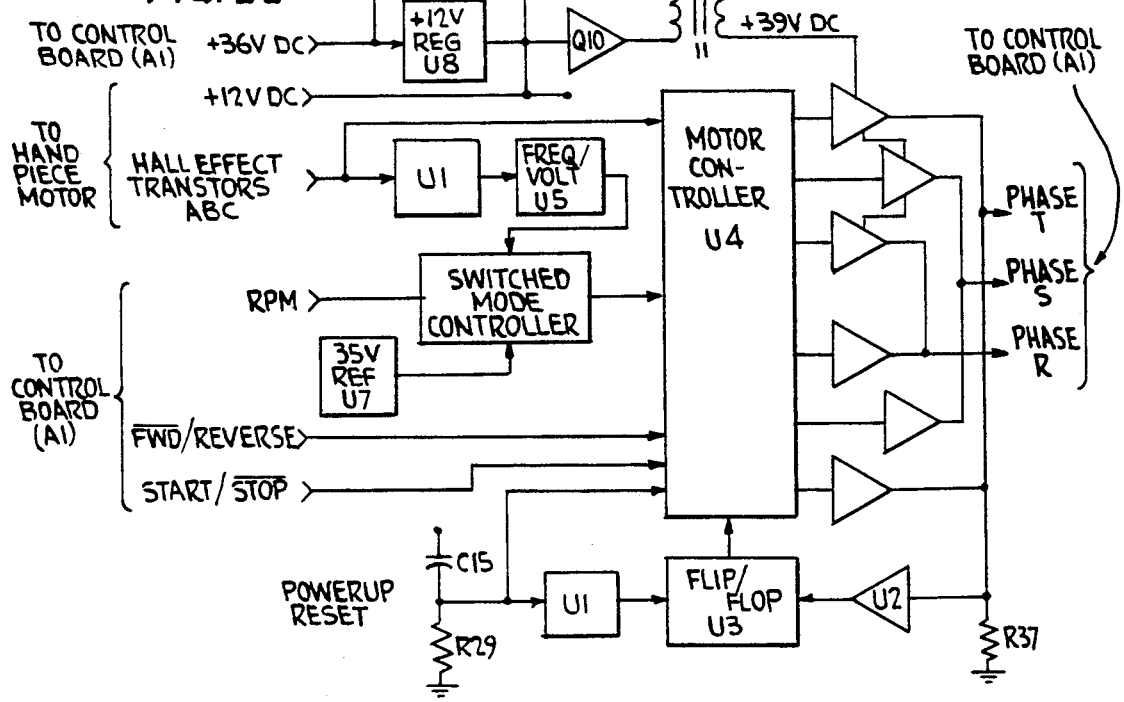
FIG. 22 is a functional block diagram of the motor drive assembly located in the control console.
Figure 21A:
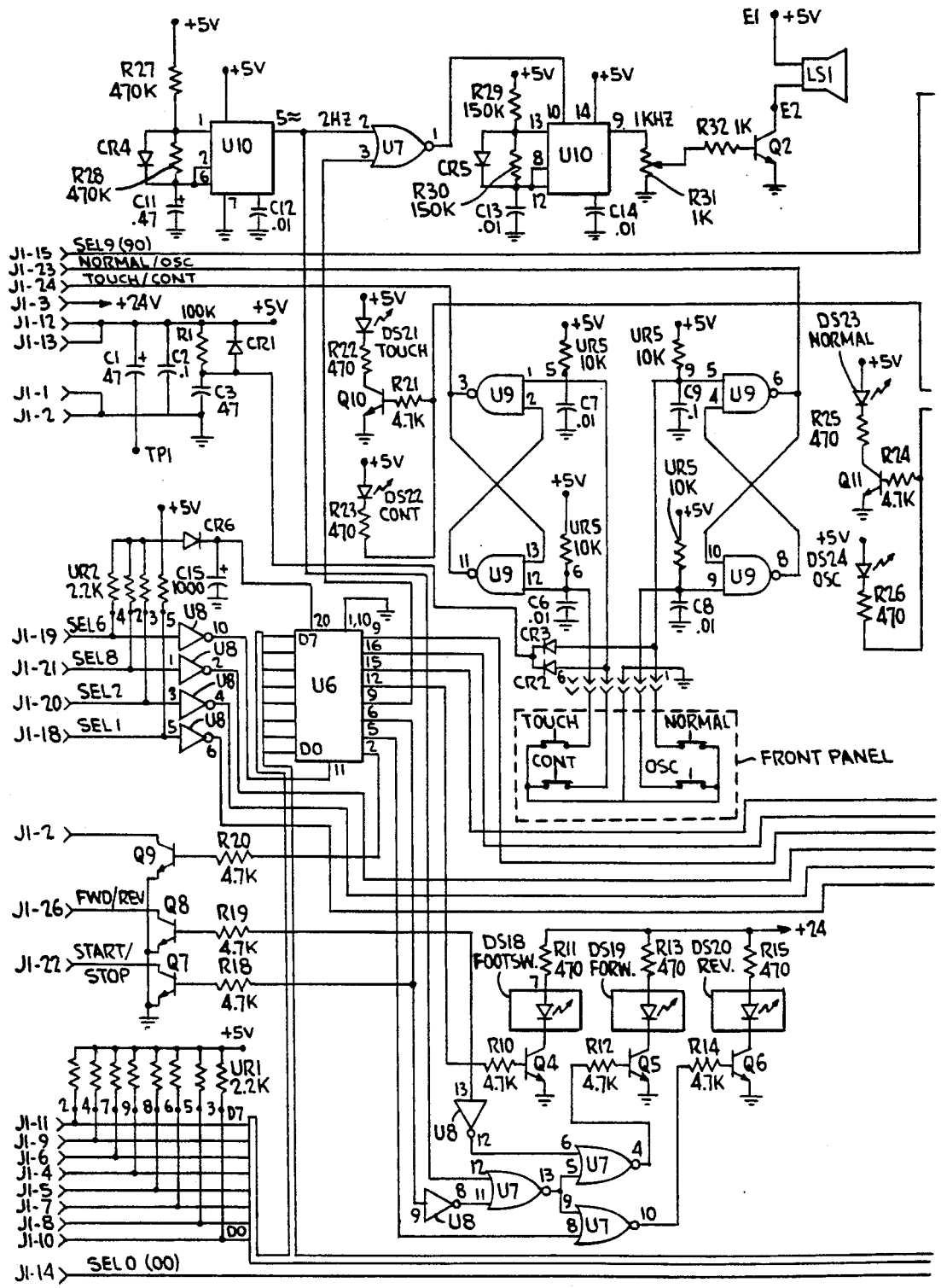
FIG. 21A and 21B are a detailed schematic diagram of the display board.
Figure 21B:
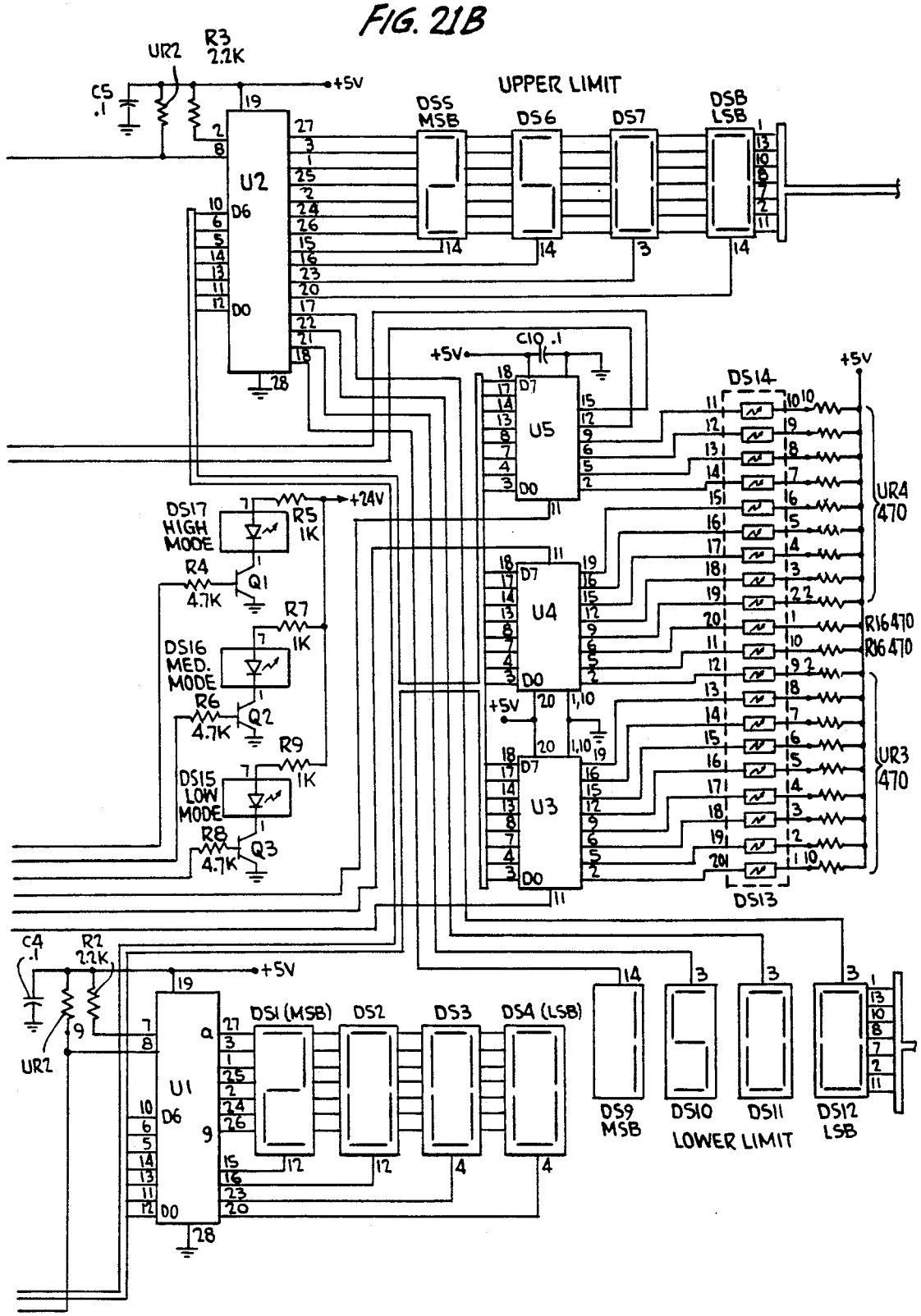
Figure 23A:
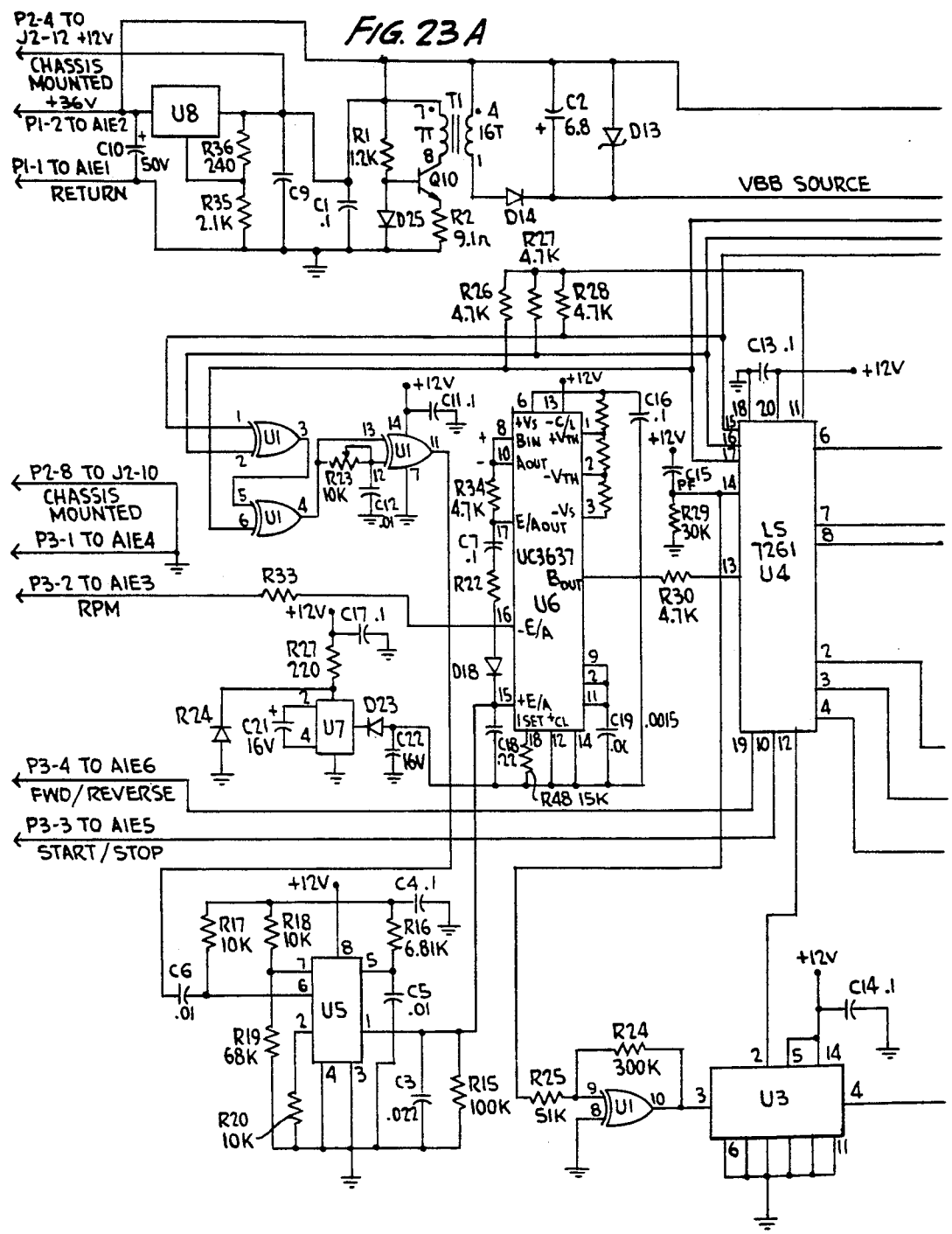
FIG. 23A and 23B are a detailed schematic diagram of the motor drive assembly.
Figure 23B:
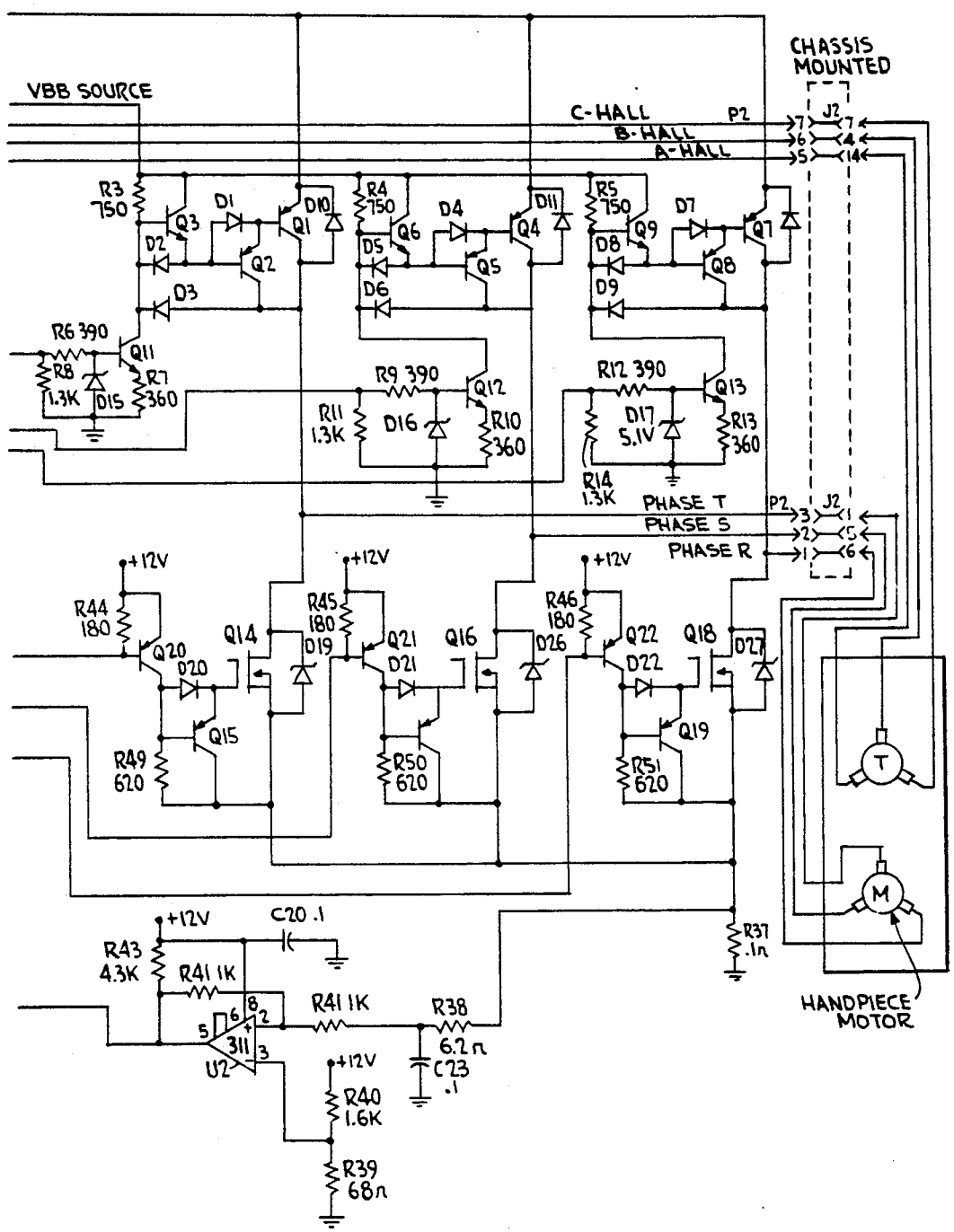

The electronic components are provided on three circuit boards, namely the control board illustrated in FIGS. 18 and 19, the display board illustrated in FIGS. 20 and 21, and the motor drive assembly illustrated in FIGS. 22 and 23. The circuitry present on each of these circuit boards is described below. Referring first to the electrical schematic diagram in FIG. 18 and the functional block diagram in FIG. 19 for the control board, it will be seen that the control board includes four sections, namely, the power supplies, the microprocessor, the signal input section, and the digital-to-analog output section. The power supply section furnishes two regulated d.c. voltages of +5 volts and +12 volts for internal circuit requirements. It also provides an unregulated d.c. +36 volts for the handpiece drive unit. The system is internally wired for a nominal 115 volts 50/60 Hz operation. Mains transformer T1 has a multiple-tap primary winding for 100, 110 and 120 volt operation, or 200, 220 and 240 volt operation. The mains power is supplied to transformer T1 via jack J1, circuit breakers CB1 (and CB2 for 230 volts a.c. units) and mains power switch S1. Transformer T1 includes three secondary windings for providing 9.2 volts, 18 volts and 28 volts. The 28 volts a.c. winding is fused by a fuse F1, rectified by bridge CR1-CR4 and filtered by capacitor C1. The unregulated +36 volts d.c. is used to drive motor 51 in the handpiece. The 18 volts a.c. winding is fused by fuse F3 and rectified by bridge BR1. Capacitor C5 serves to filter this voltage which is regulated +12 volts d.c. by voltage regulator VR2. The 9.2 volts a.c. winding is fused by fuse F2 and rectified by bridge rectifier CR5-CR8. The rectified voltage is filtered by capacitor C2 and regulated to +5 volts d.c. via voltage regulator VR1.

The CPU section contains a Z-80 type microprocessor with 1 Kbyte of random access memory, 4 Kbytes of EPROM memory, a reset circuit, clock, address decoders and the line driver/buffer circuit. The Z-80 microprocessor U1 is clocked at 4 MHz by a quartz crystal controlled oscillator U2.

The program monitor reset circuit in the CPU section includes a dual timer U10, NAND gates U8, U9, and transistors Q1, Q2. These components provide the power "on" reset and cause a system restart if the processor jumps to an illegal address or becomes caught in a programming loop. Switch S1 may be utilized for trouble shooting purposes when in the "inhibit" position, reset pulses are disconnected from the CPU integrated circuit U1. The system may be manually started by momentarily grounding pin 26 of CPU U1 to determine whether or not there is a problem with the program monitor unit.

Two sections of integrated circuit U8 form a cross-coupled RS flip-flop. The flip-flop is toggled each time the correct sequence of addressing is initiated by the program. The flip-flop pulses are utilized to trigger the second section of the timer U10. If the program fails to toggle the flip-flop (indicating improper program execution), capacitor C11 charges to a threshold level and triggers the timer to begin a reset pulse from the power supply section.

Transistor Q2 provides the discharge path for capacitor C11. Transistor Q1 assures full discharge of capacitor C11 by feeding back the discharge pulse to the base of transistor Q2. The time constant established by resistor R16 and capacitor C11 sets the minimum time allowed between address pulses from the program before a reset occurs. The time constant established by resistor R18 and capacitor C14 sets the reset pulse low time, and the time constant established by resistor R17 and capacitor C13 sets the "wait for initialize" time high after the restart.

Integrated circuit U4 is a 1 Kbyte random access memory utilized for stack operations and scratch pad memory purposes. Integrated circuit U5 is a 4 Kbyte EPROM in which the system program is stored. Integrated circuit U3 is a three-two-eight line decoder utilized for memory selection. Integrated circuit U7 is a four-two-sixteen line decoder providing input/output (I/O) selection for the system. The data buss is buffered from peripheral circuitry by integrated circuit U6.

The signal input section of the control board accepts commands from the handpiece, the footswitch, and from the front panel display board. Handpiece commands are RC-filtered, level-shifted by integrated circuit U17 from +12 volts to +5 volts d.c. and transferred onto the data buss via buffer U16. The RC-filtered front panel commands and the footswitch commands are transferred onto the data buss via buffer U15. The footswitch is electrically isolated from the system by optoisolators U12, U13 and U14.

The primary winding of transformer T1 is driven by transistor Q3 which is switched at a 25 KHz rate by oscillator U11. The secondary winding of transformer T1 is rectified and filtered to produce an isolated +5 volts d.c. that is then applied to the footswitch. When the footswitch is connected, it energizes optoisolator U13. When the footswitch "reverse" pedal is depressed, it energizes optoisolator U12. The forward pedal energizes optoisolator U14. The output signals from optoisolators U12, U13 and U14 are transferred onto the data buss by buffer U15.

The digital-to-analog section of the control board receives a digital word from the CPU U1 and converts it to an analog voltage that sets the motor speed via the drive assembly circuit (FIGS. 22, 23). The digital-to-analog convertor U18 converts the digital word to an analog voltage. This voltage is divided by resistors R38 and R40 and then RC-coupled to operational amplifier U19. Potentiometer R42 is used to set the maximum speed of 2500 rpm. The signal is then coupled to the offset amplifier where resistor R48 sets the minimum speed of 75 rpm. Thereafter the signal is routed to the drive assembly (FIGS. 22, 23) where it is used to set the motor speed.

The display board is illustrated in FIGS. 20 (functional block diagram) and 21 (detailed schematic). The display board controls the LED digit displays, the 5 range bar graph and all of the indicator lamps at the console front panel. Commands are provided from the display board to the drive assembly (FIGS. 22, 23), and input signals are received by the display board from the front panel switches.

Each of the LED driver integrated circuits (U1 for actual speed display 32; U2 for upper and lower limit displays 29 and 31) contain an eight-by-four bit random access memory (RAM). Data to be displayed is written as a four-bit word. The low order four bits (D0-D3) contain the number to be written, and the high order four bits (D4-D7) contain the address to the internal RAM location. Each of the four-bit words are multiplexed to the seven-segment LED's at a two kilohertz rate by a clock that is internal to the driver integrated circuit.

Output latches U3, U4 and U5 receive digital information from the CPU to drive the bar graphs DS13, DS14 and LED's DS21-DS24.

Output latch U6 receives digital information from the CPU and controls the audio, the front panel indicators DS15-DS20, and output commands to the drive assembly (FIGS. 22, 23) via the control board (FIGS. 18, 19). Transistors Q7 and Q8 are employed to level shift the voltage from +5 to +12 volts d.c.

Audio speaker LS1 is driven by transistor Q12, the latter being switched at a 500 Hz rate by one-half of oscillator U10. Potentiometer R31 is utilized to internally set the audio sound level. The other half of oscillator U10 is a two Hz oscillator used to switch the 500 Hz audio oscillator to beep the audio and to blink the forward and reverse indicators when the motor is running.

Two sections of integrated circuit U9 form a cross-coupled RS flip-flop which accepts input signals from the touch switch 23 and the continuous switch 22 located at the front panel. Flip-flop U9 also provides an output signal to the control board (FIGS. 18, 19). The other two sections of the flip-flop U9 accept input signals from the "OSC" switch 24 and the "NORM" switch 25 located at the front panel.

The motor drive assembly board is illustrated in functional block diagram form in FIG. 22 and in a detailed schematic diagram in FIG. 23. The motor drive assembly is a closed loop three-phase system used to control the brushless d.c. motor 51 located in the handpiece 11.

Voltage regulator U8 develops +12 volts d.c. for internal circuit requirements and is also employed by the motor position sensors. Transistor Q10, transformer T1 and associated components are employed to develop a voltage which is +3 volts d.c. higher than the voltage present at pin 2 of plug P1. This higher voltage is employed to turn off transistors Q1, Q4 and Q7. In addition, a −3.5 volts d.c. reference voltage is generated by voltage convertor U7 so as to be utilized by the switched mode controller U6.

There are three Hall effect transistors (A,B,C) located in motor 51 and serve to relay the motor position information to the motor controller U4. This information, along with the speed data information supplied by the switched-mode controller U6, is employed to provide electronic commutations of the motor windings. The three phases R, S and T are driven by the bipolar and field effect transistor switching output stages Q1-Q9 and Q11-Q22.

Over current circuitry is provided to protect the windings, the associated drivers, and the power supply. Voltage comparator U2 senses the voltage across resistor R37. If this voltage exceeds the preset limit, +12 volts is applied to motor controller U4 (at pin 12) via flip-flop U13 to disable the output signals. One-quarter of exclusive OR gate U1 is employed during the power-up state to supply a ground reference to the motor controller U4 (at pin 12) via flip-flop U13 for normal operation.

The Hall effect transistor signals from the motor are also used for velocity feedback in the closed loop system. These signals are combined and waved-shaped by exclusive OR gate U1 and applied to the frequency-to-voltage convertor U5. This d.c. voltage is then sent to the switched mode controller U6 which compares the voltage at pin 6 (rpm commanded from the control board) with the voltage at pin 15 (actual motor speed). This signal difference is then applied to the motor controller U4 to maintain a constant speed.

It is to be understood that the various specific dimensions presented by way of example herein are intended to be only exemplary unless otherwise stated.

From the foregoing description it will be appreciated that the invention makes available a novel drive system for an arthroscopic surgical instrument wherein the drive motor may be entirely controlled from the handpiece and wherein automatic speed range control is effected by directly coding the cutting blade assembly and thereby eliminating the need for an intermediate adapter. The unique arcuate printed circuit board, serving as part of the handpiece control switch cluster, permits that cluster to be contoured to fit generally within the contour of the handpiece so that the handpiece itself may be more easily manipulated and so that the individual switches in the switch cluster may be quickly and accurately accessed.

Having described a preferred embodiment of a new and improved electrosurgical instrument constructed in accordance with the present invention, it is believed that other modifications, variations and changes will be suggested to those skilled in the art in view of the techniques set forth herein. It is therefore to be understood that all such variations, modifications and changes are believed to fall within the scope of the present invention as defined in the appended claims.

APPENDIX I

This appendix contains a list of parts, with components values, employed in the electronic circuitry present in the control console 10. The list of components is divided into three sections representing the three circuit boards, respectively, described herein.

| Description | Reference Designator |
|---|---|
| Control Board Assy. | A1 |
| Capacitor .001 mfd 200 V | C10, 16 |
| Capacitor .01 mfd 100 V | C12, 15, 17, 19, 21, 22, 23 |
| Capacitor .1 mfd 50 V | C4, 7-9, 11, 13, 14, 18, 24-38 |
| Capacitor 10 mfd 50 V | C20 |
| Capacitor 470 mfd 35 V | C6 |
| Capacitor 1000 mfd 35 V | C3, 5 |
| Capacitor 4700 mfd 25 V | C2 |
| Capacitor 4700 mfd 50 V | C1 |
| Rectifier, Bridge 2 Amp | BR1 |
| Diode 3 amp 200 V | CR1-8 |

-continued

| Description | Reference Designator |
|---|---|
| Diode 1N4001 | CR11-19 |
| Suppressor 5 V | CR9 |
| Suppressor 12 V | CR10 |
| L.E.D. red | DS1-3 |
| Fuse 2.5 amp Slow | F1 |
| Fuse 2 amp Slow | F2 |
| Fuse ¼ amp Slow | F3 |
| Clips, Fuse | XF1, F2, F3 |
| I.C. C.P.U. MK 3880N-4 | U1 |
| I.C. OSC. M1259-4M | U2 |
| I.C. 3-8 decoder 74LS138 | U3 |
| I.C. RAM MK4801AN-3 | U4 |
| I.C. EPROM 2732A Oper. Prog. | U5 |
| I.C. Buffer 74LS245 | U6, 15, 16 |
| I.C. 4-16 decoder 74LS154 | U7 |
| I.C. Nand gate 74LS132 | U8, 9 |
| I.C. Timer 556 | U10 |
| I.C. Timer 555 | U11 |
| I.C. Optoisolator 4N38A | U12, 13, 14 |
| I.C. Inverter 4049 | U17 |
| I.C. D/A converter AD448JN | U18 |
| I.C. Op Amp LM358 | U19 |
| I.C. Nand gate 4093 | U20 |
| I.C. Inverter 74HC4049 | U21 |
| Resistor 39, 5% ¼ w | R23 |
| Resistor 47, 5% ¼ w | R24-26 |
| Resistor 100, 5% ¼ w | R14, 24-26 |
| Resistor 120, 5% ¼ w | R4 |
| Resistor 220, 5% ¼ w | R22 |
| Resistor 270, 5% ¼ w | R3 |
| Resistor 1K, 5% ¼ w | R5, 7, 8, 11, 15, 30, 31 |
| Resistor 2.2K, 5% ¼ w | R6, 9 |
| Resistor 4.7K, 5% ¼ w | R13, 27-29, 38, 40 |
| Resistor 6.8K, 5% ¼ w | R1, 19 |
| Resistor 10K, 5% ¼ w | R10, 12, 21, 32-37, 39, 49-52 |
| Resistor 22K, 5% ¼ w | R20 |
| Resistor 68K, 5% ¼ w | R43 |
| Resistor 100K, 5% ¼ w | R41, 44-47 |
| Resistor 220K, 5% ¼ w | R17, 18 |
| Resistor 1M, 5% ¼ w | R16, 53 |
| Resistor Network 2.2K | UR1-3 |
| Resistor Network 10K | UR4 |
| Potentiometer 200 | R2 |
| Potentiometer 1K | R48 |
| Potentiometer 50K | R42 |
| Regulator, Adj. LM350K, +5 V | VR1 |
| Regulator, LM340T12, +12 V | VR2 |
| Switch SPDT Slide | S1 |
| Transistor, PN2222A NPN | Q1, 2, 4 |
| Transistor, 2N3019 NPN | Q3 |
| Transformer, Isolation | T1 |
| Plug Housing 2 position | A3P1 |
| Plug Housing 4 position | A3P3 |
| Contact, Leaf | X A3P1, A3P3 |
| Header, 4 pin | J4 |
| Header, 7 pin | J2 |
| Header, 26 pin Rt. Ang. | J1 |
| Receptacle, 6 pin | J3 |
| Key, Header polarization | XJ1 |
| Heatsink T0-3 | XVR1 |
| Heatsink T0-5 | XQ3 |
| Heatsink T0-220 | XVR2 |
| Mount, 14 Pin Dip | XU2 |
| Terminal, Turret | E1-8, TP1-7 |
| Mount, T05 | XQ3 |
| Display Board Assy | A2 |
| Cable Assembly - 26 Pin | J1 |
| Capacitor .01 mfd 100 V | C6-9, 12-14 |
| Capacitor .1 mfd 50 V | C2, 4-5, 10 |
| Capacitor .47 mfd 35 V | C3, C11 |
| Capacitor 47 mfd 25 V | C1 |
| Diode 1N4001 | CR1, 4, 5 |
| Diode 1N277 | CR2, 3 |
| Display, 7 segment (.8") HDSP-3900 | DS1-4 |
| Display, 7 segment (.3") 5082-7730 | DS5-12 |
| LED, Red bar graph, HDSP-4820 | DS13, 14 |
| LED, Red light bar HLMP-2685 | DS15-17 |
| LED, Yel light bar HLMP-2785 | DS18 |
| LED, Grn light bar HLMP-2885 | DS19, 20 |

-continued

| Description | Reference Designator |
|---|---|
| LED, Red | DS21-24 |
| I.C. LED driver, ICM 7218CIJI | U1, 2 |
| I.C. Latch, 74LS373 | U3-5 |
| I.C. Latch, 74HC373 | U6 |
| I.C. Norgate, 74LS02 | U7 |
| I.C. Inverter, 74LS04 | U8 |
| I.C. Nandgate, 74HC132 | U9 |
| I.C. Timer, 556 | U10 |
| Transistor PN2222A NPN | Q1-12 |
| Resistor, 470, 5% ¼ w | R11, 13, 15, 16, 17, 22, 23, 25, 26 |
| Resistor, 1K, 5% ¼ w | R5, 7, 9, 32 |
| Resistor, 2.2K, 5% ¼ w | R2, 3 |
| Resistor, 4.7K, 5% ¼ w | R4, 6, 8, 10, 12, 14, 18-21, 24 |
| Resistor, 100K, 5% ¼ w | R1 |
| Resistor, 150K, 5% ½ | R29, 30 |
| Resistor, 470K 5% ¼ w | R27, 28 |
| Resistor, network 470 | UR3, 4 |
| Resistor, network 2.2K | UR1, 2 |
| Resistor, network 10K | UR5 |
| Potentiometer, 1K | R31 |
| Header, 6 Pin | J2 |
| Mount, 16 Pin .3 | XDS13-20 |
| Speaker 8 ohm | LS1 |
| Capacitor 680 pfd Ceramic | C15 |
| Capacitor .0015 mfd Ceramic | C19 |
| Capacitor .01 mfd Ceramic | C5, 6 12 |
| Capacitor .022 mfd Ceramic | C3 |
| Capacitor .1 mfd Ceramic | C1, 4, 7, 8, 11, 13, 14, 16, 17, 20, 23 |
| Capacitor .22 mfd Ceramic | C18 |
| Capacitor 1.5 mfd 6 V Tantalum | C9 |
| Capacitor 6.8 mfd 6 V Tantalum | C2 |
| Capacitor 100 mfd 16 V Electrolytic | C21, 22 |
| Capacitor 330 mfd 50 V Electrolytic | C10 |
| Diode IN4148 | D1-9, 14, 18, 20, 21, 22, 25 |
| Diode IN4001 50 V 1 amp | D23 |
| Diode MUR805 50 V 8 amp | D10-12 |
| Diode IN5225 3 V Zener .5 w | D13 |
| Diode IN4732B 4.7 V Zener .5 w | D24 |
| Diode IN5231 5.1 V Zener .5 w | D15-17 |
| Diode IN4754A 39 V Zener 1 w | D19, 26, 27 |
| I.C. EX-OR Gate 4070 | U1 |
| I.C. Volt. Comparator LM311 | U2 |
| I.C. Flip-Flop 4013 | U3 |
| I.C. Motor controller S7261 | U4 |
| I.C. V/Freq. converter LM331 | U5 |
| I.C. Sw-mode controller UC3637 | U6 |
| I.C. Volt. converter ICL7660CPA | U7 |
| I.C. Volt. Regulator LM317T | U8 |
| Resistor 0.1 5% 2 w | R37 |
| Resistor 6.2 5% ¼ w | R38 |
| Resistor 9.1 5% ¼ w | R2 |
| Resistor 68 5% ¼ w | R39 |
| Resistor 180 5% ¼ w | R44-46 |
| Resistor 220 5% ¼ w | R47 |
| Resistor 240 5% ¼ w | R36 |
| Resistor 360 5% ¼ w | R7, 10, 13 |
| Resistor 390 5% ¼ w | R6, 9, 12 |
| Resistor 620 5% ¼ w | R49-51 |
| Resistor 750 5% ¼ w | R3-5 |
| Resistor 1K 5% ¼ w | R41 |
| Resistor 1.2K 5% ¼ w | R1 |
| Resistor 1.3K 5% ¼ w | R8, 11, 14 |
| Resistor 1.6K 5% ¼ w | R40 |
| Resistor 2.1K 5% ¼ w | R35 |
| Resistor 3.3K 5% ¼ w | R31, 32 |
| Resistor 4.3K 5% ¼ w | R43 |
| Resistor 4.7K 5% ¼ w | R26-28, 30, 34 |
| Resistor 6.81K 1% ¼ w | R16 |
| Resistor 10K 5% ¼ w | R17, 18, 20 |
| Resistor 15K 5% ¼ w | R21, 48 |
| Resistor 30K 5% ¼ w | R29 |
| Resistor 51K 5% ¼ w | R25 |
| Resistor 68K 5% ¼ w | R19, 33 |
| Resistor 100K 5% ¼ w | R15 |
| Resistor 160K 5% ¼ w | R42 |

| Description | Reference Designator |
|---|---|
| Resistor 300K 5% ¼ w | R24 |
| Resistor 510K 5% ¼ w | R22 |
| Potentiometer 10K | R23 |
| Transistor D45H5 PNP | Q1, 4, 7 |
| Transistor ZTX750 PNP | Q2, 5, 8, 15, 17, 19 |
| Transistor 2N3904 NPN | Q3, 6, 9 |
| Transistor ZTX 650 NPN | Q10–13 |
| Transistor BUZ 71A N-CHANNEL | Q14, 16, 18 |
| Transistor 2N3906 PNP | Q20–22 |
| Transformer, Toroid | T1 |
| Connector, 2 pin | P1 |
| Connector, 4 pin | P3 |
| Connector, 8 pin | P2 |

APPENDIX II

This appendix contains a program listing for software employed in the microprocessor in an embodiment of the invention that has actually been constructed and tested. The program listing contains both object code and source code and was employed on a Z80 microprocessor.

```
LOCATION  OBJECT CODE   LINE        SOURCE LINE

1              "Z80"    LIST
                         3       ; CONCEPT, INC. - FRED REXROTH MAR 14,1986
                         4       * DWG. NO. 149-132 REV F
                         5       *
              <0006>     6       REVLEV   EQU     6         ;PROG REV LEV
              <0000>     7       SEG      DEFL    00H
              <0090>     8       SEG2     DEFL    90H
              <0010>     9       BAR1     DEFL    10H
              <0020>    10       BAR2     DEFL    20H
              <0080>    11       BAR3     DEFL    80H
              <0030>    12       DAC      DEFL    30H
              <0040>    13       FSW      DEFL    40H
              <0050>    14       HSW      DEFL    50H
              <0060>    15       LITE     DEFL    60H
                        16       ***
                        17                EXT     FLOT
                        18                EXT     FIXX
                        19                EXT     FMPY
                        20                ORG     0000H
0000 DD2143FF           21                LD      IX,43FFH  ;SP ADR
0004 DDF9               22                LD      SP,IX
0006 F3                 23                DI                ;NO INTERRUPT
0007 210001             24                LD      HL,0001H
000A 224017             25                LD      [CTR5],HL
000D 3E08               26                LD      A,8
000F 324016             27                LD      [CTR4],A
0012 3E00               28                LD      A,00H
0014 324000             29                LD      [INBUF],A
0017 32400F             30                LD      [FLAGS],A
001A D330               31                OUT     [DAC],A
001C CD0778             32                CALL    CHECK     ;LIGHTS TEST
001F C300AC             33                JP      MOTOK
0022 DB40               34       IDLE     IN      A,[FSW]
0024 CB47               35                BIT     0,A
0026 200F               36                JR      NZ,NOFSW  ;FSW IN ?
0028 3A4000             37                LD      A,[INBUF] ;JP IF NO
002B CBF7               38                SET     6,A
002D 324000             39                LD      [INBUF],A
0030 3A4003             40                LD      A,[OUTBUF]
0033 CBE7               41                SET     4,A
0035 180D               42                JR      JP1       ;FSW LITE ON
0037 3A4000             43       NOFSW    LD      A,[INBUF]
003A CBB7               44                RES     6,A
003C 324000             45                LD      [INBUF],A
003F 3A4003             46                LD      A,[OUTBUF]
0042 CBA7               47                RES     4,A       ;FSW LITE OFF
0044 324003             48       JP1      LD      [OUTBUF],A
0047 D360               49                OUT     [LITE],A
0049 AF                 50                XOR     A         ;ZERO A REG
004A 32401C             51                LD      [OLDINB],A
```

| LOCATION | OBJECT CODE | LINE | | SOURCE LINE | | |
|---|---|---|---|---|---|---|
| 004D | D330 | 52 | | OUT | [DAC],A | ;MIN RPM |
| 004F | 3A4003 | 53 | | LD | A,[OUTBUF] | |
| 0052 | CB97 | 54 | | RES | 2,A | ;ACTIVATE STOP |
| 0054 | 324003 | 55 | | LD | [OUTBUF],A | |
| 0057 | D360 | 56 | | OUT | [LITE],A | ;STOP |
| 0059 | 328000 | 57 | OPER | LD | [8000H],A | |
| 005C | 326000 | 58 | | LD | [6000H],A | |
| 005F | DB40 | 59 | | IN | A,[FSW] | |
| 0061 | CB6F | 60 | | BIT | 5,A | ;MOT CB TRIP |
| 0063 | 2847 | 61 | | JR | Z,MOTOK | ;NO,JP |
| 0065 | 0E00 | 62 | | LD | C,SEG | |
| 0067 | 3A400F | 63 | | LD | A,[FLAGS] | |
| 006A | CB67 | 64 | | BIT | 4,A | ;DSPLY TO ZERO ? |
| 006C | 2812 | 65 | | JR | Z,SETZ | ;YES JP |
| 006E | 3E00 | 66 | | LD | A,00H | |
| 0070 | ED79 | 67 | | OUT | [C],A | |
| 0072 | 3E10 | 68 | | LD | A,10H | |
| 0074 | ED79 | 69 | | OUT | [C],A | |
| 0076 | 3E20 | 70 | | LD | A,20H | |
| 0078 | ED79 | 71 | | OUT | [C],A | |
| 007A | 3E30 | 72 | | LD | A,30H | |
| 007C | ED79 | 73 | | OUT | [C],A | |
| 007E | 1810 | 74 | | JR | CKCTR | |
| 0080 | 3E0F | 75 | SETZ | LD | A,0FH | |
| 0082 | ED79 | 76 | | OUT | [C],A | |
| 0084 | 3E1F | 77 | | LD | A,1FH | |
| 0086 | ED79 | 78 | | OUT | [C],A | |
| 0088 | 3E2F | 79 | | LD | A,2FH | |
| 008A | ED79 | 80 | | OUT | [C],A | |
| 008C | 3E3F | 81 | | LD | A,3FH | |
| 008E | ED79 | 82 | | OUT | [C],A | |
| 0090 | 2A4017 | 83 | CKCTR | LD | HL,[CTR5] | |
| 0093 | 2B | 84 | | DEC | HL | |
| 0094 | 224017 | 85 | | LD | [CTR5],HL | |
| 0097 | 7C | 86 | | LD | A,H | |
| 0098 | B5 | 87 | | OR | L | |
| 0099 | 2087 | 88 | | JR | NZ,IDLE | |
| 009B | 3A400F | 89 | RLOAD | LD | A,[FLAGS] | |
| 009E | EE10 | 90 | | XOR | 10H | |
| 00A0 | 32400F | 91 | | LD | [FLAGS],A | |
| 00A3 | 210FFF | 92 | | LD | HL,0FFFH | |
| 00A6 | 224017 | 93 | | LD | [CTR5],HL | |
| 00A9 | C30022 | 94 | | JP | IDLE | |
| 00AC | CD00D0 | 95 | MOTOK | CALL | RANGE | ;SET SPEED RANGE |
| 00AF | CD016D | 96 | | CALL | SPDX | ;SPEED CHANGE |
| 00B2 | CD031C | 97 | | CALL | MODE | ;MOTOR DIR |
| 00B5 | CD04CB | 98 | | CALL | BNBCD | ;DECIMAL SPEED |
| 00B8 | CD0523 | 99 | | CALL | DISP | ;DIGITS/LITES |
| 00BB | FD210300 | 100 | | LD | IY,0300H | |
| 00BF | CD0652 | 101 | | CALL | WAIT | |
| 00C2 | 3A4000 | 102 | | LD | A,[INBUF] | |
| 00C5 | CB67 | 103 | | BIT | 4,A | ;? RUN MOTOR |
| 00C7 | CA0022 | 104 | | JP | Z,IDLE | |
| 00CA | CD0665 | 105 | | CALL | RUN | |
| 00CD | C30059 | 106 | | JP | OPER | |
| | | 107 | * | | | |
| | | 108 | *** SUBROUTINE TO SET SPEED RANGE *** | | | |
| 00D0 | 214000 | 109 | RANGE | LD | HL,INBUF | |
| 00D3 | 7E | 110 | | LD | A,[HL] | |
| 00D4 | CB7F | 111 | | BIT | 7,A | ;FULL SPD RNG ? |
| 00D6 | C0 | 112 | | RET | NZ | ;RET IF YES |
| 00D7 | DD214001 | 113 | | LD | IX,SPLB | |
| 00DB | DB50 | 114 | | IN | A,[HSW] | |
| 00DD | E603 | 115 | | AND | 03H | ;MASK |

| LOCATION | OBJECT CODE | LINE | SOURCE LINE | | | |
|---|---|---|---|---|---|---|
| 00DF | 47 | 116 | | LD | B,A | |
| 00E0 | 7E | 117 | | LD | A,[HL] | |
| 00E1 | E603 | 118 | | AND | 03H | ;CP OLD CODE |
| 00E3 | B8 | 119 | | CP | B | |
| 00E4 | C8 | 120 | | RET | Z | |
| 00E5 | 78 | 121 | | LD | A,B | |
| 00E6 | FE00 | 122 | | CP | 00H | ;?SHAVER |
| 00E8 | 2013 | 123 | | JR | NZ,RESCT | |
| 00EA | 110891 | 124 | | LD | DE,LORNG | ;SET HI LO LIM |
| 00ED | CD015C | 125 | | CALL | DIGITS | |
| 00F0 | 1100EB | 126 | FALT | LD | DE,235D | |
| 00F3 | DD7300 | 127 | | LD | [IX+0],E | |
| 00F6 | DD7201 | 128 | | LD | [IX+1],D | |
| 00F9 | 3E0C | 129 | | LD | A,0CH | |
| 00FB | 77 | 130 | | LD | [HL],A | |
| 00FC | C9 | 131 | | RET | | |
| 00FD | FE02 | 132 | RESCT | CP | 02H | ;?RESECTOR |
| 00FF | 2016 | 133 | | JR | NZ,BURR | |
| 0101 | 110899 | 134 | | LD | DE,MIDRNG | ;SET HI LO LIM |
| 0104 | CD015C | 135 | | CALL | DIGITS | |
| 0107 | 1102BC | 136 | | LD | DE,0700D | |
| 010A | DD7300 | 137 | | LD | [IX+0],E | |
| 010D | DD7201 | 138 | | LD | [IX+1],D | |
| 0110 | 3E0E | 139 | | LD | A,0EH | |
| 0112 | 77 | 140 | | LD | [HL],A | |
| 0113 | CD0131 | 141 | | CALL | FWDBIT | |
| 0116 | C9 | 142 | | RET | | |
| 0117 | FE01 | 143 | BURR | CP | 01H | ;?BURR |
| 0119 | 20D5 | 144 | | JR | NZ,FALT | |
| 011B | 1108A1 | 145 | | LD | DE,HIRNG | ;SET HI LO LIM |
| 011E | CD015C | 146 | | CALL | DIGITS | |
| 0121 | 1107D0 | 147 | | LD | DE,2000D | |
| 0124 | DD7300 | 148 | | LD | [IX+0],E | |
| 0127 | DD7201 | 149 | | LD | [IX+1],D | |
| 012A | 3E0D | 150 | | LD | A,0DH | |
| 012C | 77 | 151 | | LD | [HL],A | |
| 012D | CD0131 | 152 | | CALL | FWDBIT | |
| 0130 | C9 | 153 | | RET | | |
| | | 154 | * | | | |
| 0131 | 3A4000 | 155 | FWDBIT | LD | A,[INBUF] | |
| 0134 | CBD7 | 156 | | SET | 2,A | ;SET MOT FWD |
| 0136 | 324000 | 157 | | LD | [INBUF],A | |
| 0139 | 210150 | 158 | | LD | HL,OUTF | |
| 013C | 180B | 159 | | JR | CKMOT | |
| 013E | 3A4000 | 160 | REVBIT | LD | A,[INBUF] | |
| 0141 | CB97 | 161 | | RES | 2,A | ;SET MOT REV |
| 0143 | 324000 | 162 | | LD | [INBUF],A | |
| 0146 | 210154 | 163 | | LD | HL,OUTR | |
| 0149 | 3A4003 | 164 | CKMOT | LD | A,[OUTBUF] | |
| 014C | CB57 | 165 | | BIT | 2,A | ,MOT ON ? |
| 014E | C0 | 166 | | RET | NZ | ;RET IF YES |
| 014F | E9 | 167 | | JP | [HL] | |
| 0150 | CBCF | 168 | OUTF | SET | 1,A | |
| 0152 | 1802 | 169 | | JR | OLITE | |
| 0154 | CB8F | 170 | OUTR | RES | 1,A | |
| 0156 | 324003 | 171 | OLITE | LD | [OUTBUF],A | |
| 0159 | D360 | 172 | | OUT | [LITE],A | |
| 015B | C9 | 173 | | RET | | |
| | | 174 | * | | | |
| | | 175 | *** SUBROUTINE TO DRIVE 7 SEGMENT DISPLAYS | | | |
| 015C | 0E90 | 176 | DIGITS | LD | C,SEG2 | |
| 015E | 0600 | 177 | | LD | B,00H | |
| 0160 | 210008 | 178 | | LD | HL,08H | |
| 0163 | CD0586 | 179 | NXTDIG | CALL | DIGIT | |
| 0166 | 2D | 180 | | DEC | L | |

LOCATION OBJECT CODE LINE       SOURCE LINE

```
0167 20FA           181           JR      NZ,NXTDIG
0169 214000         182           LD      HL,INBUF
016C C9             183           RET
                    184 *** SUBROUTINE TO CHANGE SPEED ***
016D DD214001       185 SPDX      LD      IX,SPLB
0171 DB50           186           IN      A,[HSW]
0173 47             187           LD      B,A             ;SAVE
0174 CB6F           188           BIT     5,A             ;?SPEED UP
0176 CA0265         189           JP      Z,SPDN          ;NO,JP
0179 DD6E00         190           LD      L,[IX+0]
017C DD6601         191           LD      H,[IX+1]
017F 3A4000         192           LD      A,[INBUF]       ;TEST RANGE
0182 E683           193           AND     83H
0184 FE00           194           CP      00H             ;LO RANGE ?
0186 205B           195           JR      NZ,MIDR         ;NO, JUMP
0188 110190         196           LD      DE,0400D
018B ED52           197           SBC     HL,DE           ;HI LIM ?
018D 2038           198           JR      NZ,SPDUP        ;NO,JP
018F CD0310         199           CALL    AUDOFF
0192 3A4000         200           LD      A,[INBUF]
0195 CB7F           201           BIT     7,A             ;FULL SPD RNG ACTV ?
0197 C0             202           RET     NZ              ;YES,JP
0198 FD21FFFF       203           LD      IY,0FFFFH
019C CD0652         204           CALL    WAIT
019F CD0652         205           CALL    WAIT
01A2 CD0652         206           CALL    WAIT
01A5 DB50           207           IN      A,[HSW]
01A7 CB6F           208           BIT     5,A             ;RPM UP SW ACTV ?
01A9 C8             209           RET     Z               ;NO,RET
01AA 214000         210           LD      HL,INBUF
01AD DD214001       211           LD      IX,SPLB
01B1 1108A9         212           LD      DE,FULRNG
01B4 CD015C         213           CALL    DIGITS
01B7 1104E2         214           LD      DE,1250D
01BA DD7300         215           LD      [IX+0],E
01BD DD7201         216           LD      [IX+1],D
01C0 3E8C           217           LD      A,08CH
01C2 77             218           LD      [HL],A
01C3 CD0131         219           CALL    FWDBIT          ;SET FWD DIR
01C6 C9             220           RET
01C7 DD6E00         221 SPDUP     LD      L,[IX+0]
01CA DD6601         222           LD      H,[IX+1]
01CD 23             223           INC     HL
01CE DD7500         224           LD      [IX+0],L
01D1 DD7401         225           LD      [IX+1],H
01D4 3A4000         226           LD      A,[INBUF]
01D7 CBAF           227           RES     5,A             ;CANCEL JOG
01D9 324000         228           LD      [INBUF],A
01DC CD0305         229           CALL    AUDON
01DF CD02F0         230           CALL    SPEED
01E2 C9             231           RET
01E3 FE02           232 MIDR      CP      02H
01E5 201C           233           JR      NZ,HIR
01E7 110384         234           LD      DE,0900D        ;HI LIMIT
01EA ED52           235           SBC     HL,DE           ;MAX RPM ?
01EC F20310         236           JP      P,AUDOFF
01EF DD6E00         237           LD      L,[IX+0]
01F2 DD6601         238           LD      H,[IX+1]
01F5 23             239           INC     HL
01F6 DD7500         240           LD      [IX+0],L
01F9 DD7401         241           LD      [IX+1],H
01FC CD0305         242           CALL    AUDON
01FF CD02F0         243           CALL    SPEED           ;DELAY
0202 C9             244           RET
0203 1109C4         245 HIR       LD      DE,2500D
```

| LOCATION | OBJECT CODE | LINE | | SOURCE LINE | | |
|---|---|---|---|---|---|---|
| 0206 | 37 | 246 | | SCF | | |
| 0207 | 3F | 247 | | CCF | | |
| 0208 | ED52 | 248 | | SBC | HL,DE | |
| 020A | 203D | 249 | | JR | NZ,RPMUP | |
| 020C | CD0310 | 250 | | CALL | AUDOFF | |
| 020F | 3A4000 | 251 | | LD | A,[INBUF] | |
| 0212 | CB7F | 252 | | BIT | 7,A | ;FULL SPD RNG ? |
| 0214 | C8 | 253 | | RET | Z | ;RET IF NO |
| 0215 | DB50 | 254 | | IN | A,[HSW] | |
| 0217 | CB6F | 255 | | BIT | 5,A | ;RPM UP ACTV ? |
| 0219 | C8 | 256 | | RET | Z | ;RET,IF NO |
| 021A | FD21FFFF | 257 | | LD | IY,0FFFFH | |
| 021E | CD0652 | 258 | | CALL | WAIT | |
| 0221 | CD0652 | 259 | | CALL | WAIT | |
| 0224 | CD0652 | 260 | | CALL | WAIT | |
| 0227 | DB50 | 261 | | IN | A,[HSW] | |
| 0229 | CB6F | 262 | | BIT | 5,A | ;RPM UP ACTV ? |
| 022B | C8 | 263 | | RET | Z | ;RET IF NO |
| 022C | 214000 | 264 | | LD | HL,INBUF | |
| 022F | DD214001 | 265 | | LD | IX,SPLB | |
| 0233 | 110891 | 266 | | LD | DE,LORNG | |
| 0236 | CD015C | 267 | | CALL | DIGITS | |
| 0239 | 1100EB | 268 | | LD | DE,235D | |
| 023C | DD7300 | 269 | | LD | [IX+0],E | |
| 023F | DD7201 | 270 | | LD | [IX+1],D | |
| 0242 | 3E0C | 271 | | LD | A,0CH | |
| 0244 | 77 | 272 | | LD | [HL],A | |
| 0245 | CD0131 | 273 | | CALL | FWDBIT | |
| 0248 | C9 | 274 | | RET | | |
| 0249 | DD6E00 | 275 | RPMUP | LD | L,[IX+0] | |
| 024C | DD6601 | 276 | | LD | H,[IX+1] | |
| 024F | 23 | 277 | | INC | HL | |
| 0250 | DD7500 | 278 | | LD | [IX+0],L | |
| 0253 | DD7401 | 279 | | LD | [IX+1],H | |
| 0256 | 3A4000 | 280 | | LD | A,[INBUF] | ;CANCEL JOG |
| 0259 | CBAF | 281 | | RES | 5,A | |
| 025B | 324000 | 282 | | LD | [INBUF],A | |
| 025E | CD0305 | 283 | | CALL | AUDON | |
| 0261 | CD02F0 | 284 | | CALL | SPEED | |
| 0264 | C9 | 285 | | RET | | |
| 0265 | CB67 | 286 | SPDN | BIT | 4,A | ;SP DOWN? |
| 0267 | CA0310 | 287 | | JP | Z,AUDOFF | ;NO JP |
| 026A | DD5E00 | 288 | | LD | E,[IX+0] | |
| 026D | DD5601 | 289 | | LD | D,[IX+1] | |
| 0270 | 3A4000 | 290 | | LD | A,[INBUF] | |
| 0273 | E683 | 291 | | AND | 83H | |
| 0275 | FE01 | 292 | | CP | 01H | ;HI RNG ? |
| 0277 | 2018 | 293 | | JR | NZ,MRDN | ;NO,JP |
| 0279 | 2105DC | 294 | | LD | HL,1500D | |
| 027C | 37 | 295 | | SCF | | |
| 027D | 3F | 296 | | CCF | | |
| 027E | ED52 | 297 | | SBC | HL,DE | |
| 0280 | CA0310 | 298 | | JP | Z,AUDOFF | |
| 0283 | 1B | 299 | | DEC | DE | |
| 0284 | DD7300 | 300 | | LD | [IX+0],E | |
| 0287 | DD7201 | 301 | | LD | [IX+1],D | |
| 028A | CD0305 | 302 | | CALL | AUDON | |
| 028D | CD02F0 | 303 | | CALL | SPEED | |
| 0290 | C9 | 304 | | RET | | |
| 0291 | FE02 | 305 | MRDN | CP | 02H | ;MED RNG ? |
| 0293 | 2018 | 306 | | JR | NZ,LRDN | ;NO,JP |
| 0295 | 2101F4 | 307 | | LD | HL,0500D | ;LO LIMIT |
| 0298 | 37 | 308 | | SCF | | |
| 0299 | 3F | 309 | | CCF | | |
| 029A | ED52 | 310 | | SBC | HL,DE | ;SPD = LO SPD LIMIT ? |

| LOCATION | OBJECT CODE | LINE | | SOURCE LINE | | |
|---|---|---|---|---|---|---|
| 029C | CA0310 | 311 | | JP | Z,AUDOFF | ;JP IF YES |
| 029F | 1B | 312 | | DEC | DE | |
| 02A0 | DD7300 | 313 | | LD | [IX+0],E | |
| 02A3 | DD7201 | 314 | | LD | [IX+1],D | |
| 02A6 | CD0305 | 315 | | CALL | AUDON | |
| 02A9 | CD02F0 | 316 | | CALL | SPEED | |
| 02AC | C9 | 317 | | RET | | |
| 02AD | 3A4000 | 318 | LRDN | LD | A,[INBUF] | |
| 02B0 | CB6F | 319 | | BIT | 5,A | ;JOG ACTV ? |
| 02B2 | C0 | 320 | | RET | NZ | ;YES JP |
| 02B3 | 21004B | 321 | | LD | HL,075D | ;LO LIMIT |
| 02B6 | 37 | 322 | | SCF | | |
| 02B7 | 3F | 323 | | CCF | | |
| 02B8 | ED52 | 324 | | SBC | HL,DE | ;DE HAS OLD SPEED |
| 02BA | CA02CB | 325 | | JP | Z,ASP | |
| 02BD | 1B | 326 | | DEC | DE | |
| 02BE | DD7300 | 327 | | LD | [IX+0],E | |
| 02C1 | DD7201 | 328 | | LD | [IX+1],D | |
| 02C4 | CD0305 | 329 | | CALL | AUDON | |
| 02C7 | CD02F0 | 330 | | CALL | SPEED | |
| 02CA | C9 | 331 | | RET | | |
| 02CB | CD0310 | 332 | ASP | CALL | AUDOFF | |
| 02CE | FD21FF00 | 333 | | LD | IY,0FF00H | |
| 02D2 | CD0652 | 334 | | CALL | WAIT | |
| 02D5 | DB50 | 335 | | IN | A,[HSW] | |
| 02D7 | CB67 | 336 | | BIT | 4,A | ;? SPEED DN |
| 02D9 | C8 | 337 | | RET | Z | ;NO JP |
| 02DA | 3A4000 | 338 | | LD | A,[INBUF] | |
| 02DD | CBEF | 339 | | SET | 5,A | ;JOG |
| 02DF | 324000 | 340 | | LD | [INBUF],A | |
| 02E2 | 3A400E | 341 | | LD | A,[GRAPH+2] | |
| 02E5 | CBEF | 342 | | SET | 5,A | ;TOUCH LITE ON |
| 02E7 | 32400E | 343 | | LD | [GRAPH+2],A | |
| 02EA | D380 | 344 | | OUT | [BAR3],A | |
| 02EC | CD0131 | 345 | | CALL | FWDBIT | |
| 02EF | C9 | 346 | | RET | | |
| | | 347 | * | | | |
| 02F0 | FD212FFF | 348 | SPEED | LD | IY,02FFFH | |
| 02F4 | 3A4016 | 349 | | LD | A,[CTR4] | |
| 02F7 | FE00 | 350 | | CP | 00H | |
| 02F9 | F202FD | 351 | | JP | P,SLO | |
| 02FC | C9 | 352 | | RET | | ;FAST SPD EXIT |
| 02FD | 3D | 353 | SLO | DEC | A | |
| 02FE | 324016 | 354 | | LD | [CTR4],A | |
| 0301 | CD0652 | 355 | | CALL | WAIT | ;SLOW SPD EXIT |
| 0304 | C9 | 356 | | RET | | |
| | | 357 | * | | | |
| 0305 | 3A4003 | 358 | AUDON | LD | A,[OUTBUF] | |
| 0308 | CB9F | 359 | | RES | 3,A | |
| 030A | 324003 | 360 | AUDIO | LD | [OUTBUF],A | |
| 030D | D360 | 361 | | OUT | [LITE],A | |
| 030F | C9 | 362 | | RET | | |
| | | 363 | * | | | |
| 0310 | 3E08 | 364 | AUDOFF | LD | A,08D | |
| 0312 | 324016 | 365 | | LD | [CTR4],A | |
| 0315 | 3A4003 | 366 | | LD | A,[OUTBUF] | |
| 0318 | CBDF | 367 | | SET | 3,A | |
| 031A | 18EE | 368 | | JR | AUDIO | |
| | | 369 | * | | | |
| | | 370 | *** SUBROUTINE TO SET MOTOR DIRECTION *** | | | |
| 031C | DB50 | 371 | MODE | IN | A,[HSW] | |
| 031E | 5F | 372 | | LD | E,A | |
| 031F | CB47 | 373 | | BIT | 0,A | ;HI SPD RNG ? |
| 0321 | 203F | 374 | | JR | NZ,FRR | ;YES,JP |
| 0323 | DB40 | 375 | | IN | A,[FSW] | |

| LOCATION | OBJECT CODE | LINE | | SOURCE LINE | | |
|---|---|---|---|---|---|---|
| 0325 | CB5F | 376 | | BIT | 3,A | ;OSC ? |
| 0327 | 2039 | 377 | | JR | NZ,FRR | ;NO,JP |
| 0329 | 2A4001 | 378 | | LD | HL,[SPLB] | |
| 032C | 010385 | 379 | | LD | BC,901D | |
| 032F | 37 | 380 | | SCF | | |
| 0330 | 3F | 381 | | CCF | | |
| 0331 | ED42 | 382 | | SBC | HL,BC | ;SPD > 900 ? |
| 0333 | F20362 | 383 | | JP | P,FRR | ;YES,JP |
| 0336 | 3A4000 | 384 | SETOSC | LD | A,[INBUF] | |
| 0339 | CB9F | 385 | | RES | 3,A | ;SET OSC MODE |
| 033B | 324000 | 386 | | LD | [INBUF],A | |
| 033E | 3A400E | 387 | | LD | A,[GRAPH+2] | |
| 0341 | CBA7 | 388 | | RES | 4,A | |
| 0343 | 32400E | 389 | | LD | [GRAPH+2],A | |
| 0346 | D380 | 390 | | OUT | [BAR3],A | |
| 0348 | 187E | 391 | | JR | JOG | |
| 034A | FE01 | 392 | FDRV | CP | 01H | ;HI RNG |
| 034C | 2014 | 393 | | JR | NZ,FRR | ;NO,JP |
| 034E | 3A4000 | 394 | | LD | A,[INBUF] | |
| 0351 | CBDF | 395 | | SET | 3,A | ;CONT |
| 0353 | 324000 | 396 | | LD | [INBUF],A | |
| 0356 | 3A400E | 397 | | LD | A,[GRAPH+2] | |
| 0359 | CBE7 | 398 | | SET | 4,A | ;SET NORM MODE |
| 035B | 32400E | 399 | | LD | [GRAPH+2],A | |
| 035E | D380 | 400 | | OUT | [BAR3],A | |
| 0360 | 1812 | 401 | | JR | FRCHK | |
| 0362 | 3A4000 | 402 | FRR | LD | A,[INBUF] | |
| 0365 | CBDF | 403 | | SET | 3,A | ;SET CONT MODE |
| 0367 | 324000 | 404 | | LD | [INBUF],A | |
| 036A | 3A400E | 405 | | LD | A,[GRAPH+2] | |
| 036D | CBE7 | 406 | | SET | 4,A | ;SET NORM MODE |
| 036F | 32400E | 407 | | LD | [GRAPH+2],A | |
| 0372 | D380 | 408 | | OUT | [BAR3],A | |
| 0374 | 3A4000 | 409 | FRCHK | LD | A,[INBUF] | |
| 0377 | CB6F | 410 | | BIT | 5,A | ;JOG ACTV ? |
| 0379 | 204D | 411 | | JR | NZ,JOG | ;YES,JP |
| 037B | DB40 | 412 | | IN | A,[FSW] | |
| 037D | CB47 | 413 | | BIT | 0,A | ;FSW IN ? |
| 037F | 2835 | 414 | | JR | Z,FIN | ;YES,JP |
| 0381 | 3A4000 | 415 | | LD | A,[INBUF] | |
| 0384 | CBB7 | 416 | | RES | 6,A | ;RES FSW FLG |
| 0386 | 324000 | 417 | | LD | [INBUF],A | |
| 0389 | 3A400F | 418 | | LD | A,[FLAGS] | |
| 038C | CB4F | 419 | | BIT | 1,A | ;F/R FLG ACTV ? |
| 038E | C20474 | 420 | | JP | NZ,SW2ACT | ;YES JP |
| 0391 | CB53 | 421 | | BIT | 2,E | ;F/R SW ACTV ? |
| 0393 | 2833 | 422 | | JR | Z,JOG | ;NO,JP |
| 0395 | CBCF | 423 | | SET | 1,A | ;SET F/R DEB FLG |
| 0397 | 32400F | 424 | | LD | [FLAGS],A | ;SAVE FLAGS |
| 039A | 21001F | 425 | | LD | HL,01FH | ;SET DEB COUNTER |
| 039D | 224012 | 426 | | LD | [CTR2],HL | |
| 03A0 | 3A4000 | 427 | | LD | A,[INBUF] | |
| 03A3 | EE04 | 428 | | XOR | 04H | ;TOGGLE BIT 2 |
| 03A5 | 324000 | 429 | | LD | [INBUF],A | |
| 03A8 | CB57 | 430 | | BIT | 2,A | ;FWD/REV ? |
| 03AA | 2805 | 431 | | JR | Z,REV | ;JP IF REV |
| 03AC | CD0131 | 432 | | CALL | FWDBIT | ;SET FWD |
| 03AF | 1817 | 433 | | JR | JOG | |
| 03B1 | CD013E | 434 | REV | CALL | REVBIT | ;SET REV |
| 03B4 | 1812 | 435 | | JR | JOG | |
| 03B6 | 3A4000 | 436 | FIN | LD | A,[INBUF] | |
| 03B9 | CBF7 | 437 | | SET | 6,A | ;FSW FLG |
| 03BB | 324000 | 438 | | LD | [INBUF],A | |
| 03BE | 3A400E | 439 | | LD | A,[GRAPH+2] | |
| 03C1 | CBEF | 440 | | SET | 5,A | ;TOUCH MODE |

```
LOCATION  OBJECT CODE  LINE         SOURCE LINE

03C3      32400E       441              LD      [GRAPH+2],A
03C6      D380         442              OUT     [BAR3],A
03C8      3A4000       443  JOG         LD      A,[INBUF]
03CB      CB6F         444              BIT     5,A           ;? JOG MODE
03CD      2813         445              JR      Z,NOJOG       ;JP IF NO
03CF      AF           446              XOR     A
03D0      32400F       447              LD      [FLAGS],A
03D3      CD0131       448              CALL    FWDBIT
03D6      3A400E       449              LD      A,[GRAPH+2]   ;SET CONT LITE
03D9      CBE7         450              SET     4,A
03DB      32400E       451              LD      [GRAPH+2],A
03DE      D380         452              OUT     [BAR3],A
03E0      1810         453              JR      JOGIT
03E2      DB40         454  NOJOG       IN      A,[FSW]
03E4      CB67         455              BIT     4,A           ;TOUCH OR CONT ?
03E6      202C         456              JR      NZ,AONF       ;JP IF CONT
03E8      3A400E       457              LD      A,[GRAPH+2]
03EB      CBEF         458              SET     5,A
03ED      32400E       459              LD      [GRAPH+2],A
03F0      D380         460              OUT     [BAR3],A
03F2      3A4000       461  JOGIT       LD      A,[INBUF]
03F5      CB77         462              BIT     6,A           ;FSW PLUGED IN?
03F7      200D         463              JR      NZ,CKFSW      ;JP IF YES
03F9      CB5B         464              BIT     3,E           ;HSW ON/OFF ACTV ?
03FB      2809         465              JR      Z,CKFSW       ;NO,JP
03FD      3A4000       466              LD      A,[INBUF]
0400      CBE7         467              SET     4,A           ;RUN MOT
0402      324000       468              LD      [INBUF],A
0405      C9           469              RET
0406      3A4000       470  CKFSW       LD      A,[INBUF]
0409      CB77         471              BIT     6,A           ;FSW IN ?
040B      C2049C       472              JP      NZ,FONF       ;YES,JP
040E      CBA7         473              RES     4,A           ;STOP MOT
0410      324000       474              LD      [INBUF],A
0413      C9           475              RET
0414      21400F       476  AONF        LD      HL,FLAGS
0417      3A400E       477              LD      A,[GRAPH+2]
041A      CBAF         478              RES     5,A
041C      32400E       479              LD      [GRAPH+2],A
041F      D380         480              OUT     [BAR3],A
0421      CB46         481              BIT     0,[HL]        ;ON/OFF FLAG ACTIVE ?
0423      202B         482              JR      NZ,SW1ACT     ;YES,JP
0425      3A4000       483              LD      A,[INBUF]
0428      CB77         484              BIT     6,A           ;FSW ACTV ?
042A      20DA         485              JR      NZ,CKFSW      ;YES,JP
042C      CB5B         486              BIT     3,E           ;? ON/OFF ACTIVATED
042E      2005         487              JR      NZ,SWON       ;YES,JP
0430      CB5E         488              BIT     3,[HL]        ;MOT ON IN CONT MODE ?
0432      28D2         489              JR      Z,CKFSW       ;NO,JP
0434      C9           490              RET
0435      CBC6         491  SWON        SET     0,[HL]        ;SET ON/OFF DEB ACT
0437      01001F       492              LD      BC,01FH       ;INIT DEB COUNTER
043A      ED434010     493              LD      [CTR1],BC
043E      3A4000       494              LD      A,[INBUF]
0441      EE10         495              XOR     10H           ;TOGGLE BIT 4
0443      324000       496              LD      [INBUF],A
0446      CB67         497              BIT     4,A           ;MOT ON ?
0448      2003         498              JR      NZ,FLG3       ;YES,JP
044A      CB9E         499              RES     3,[HL]
044C      C9           500              RET
044D      CBDE         501  FLG3        SET     3,[HL]
044F      C9           502              RET
                       503  *
0450      ED5B4010     504  SW1ACT      LD      DE,[CTR1]     ;GET COUNT
0454      1B           505              DEC     DE
```

```
LOCATION  OBJECT CODE  LINE      SOURCE LINE 0455 7A              506           LD      A,D
0456 B3              507           OR      E          ;COUNT ZERO ?
0457 2016            508           JR      NZ,STDAT1  ;JP IF NO
0459 DB50            509           IN      A,[HSW]
045B CB5F            510           BIT     3,A        ;ON/OFF SW ACTIVE ?
045D 2807            511           JR      Z,RESET1   ;NO,JP
045F 21001F          512           LD      HL,01FH    ;HERE IF ACTIVE
0462 224010          513           LD      [CTR1],HL  ;RESET COUNT LOOP
0465 C9              514           RET
                     515  *
0466 3A400F          516  RESET1   LD      A,[FLAGS]
0469 CB87            517           RES     0,A
046B 32400F          518           LD      [FLAGS],A
046E C9              519           RET
                     520  *
046F ED534010        521  STDAT1   LD      [CTR1],DE  ;RESTORE DATA
0473 C9              522           RET
                     523  *
0474 2A4012          524  SW2ACT   LD      HL,[CTR2]  ;GET COUNT
0477 2B              525           DEC     HL
0478 7C              526           LD      A,H
0479 B5              527           OR      L          ;COUNT ZERO ?
047A 201A            528           JR      NZ,STDAT2  ;JP IF NO
047C DB50            529           IN      A,[HSW]
047E CB57            530           BIT     2,A        ;F/R SW ACTIVE ?
0480 2809            531           JR      Z,RESET2   ;NO,JP
0482 21001F          532           LD      HL,01FH
0485 224012          533           LD      [CTR2],HL  ;RESET DEB COUNTER
0488 C303C8          534           JP      JOG
                     535  *
048B 3A400F          536  RESET2   LD      A,[FLAGS]
048E CB8F            537           RES     1,A
0490 32400F          538           LD      [FLAGS],A
0493 C303C8          539           JP      JOG
                     540  *
0496 224012          541  STDAT2   LD      [CTR2],HL  ;RESTORE
0499 C303C8          542           JP      JOG
                     543  *
049C DB40            544  FONF     IN      A,[FSW]
049E CB4F            545           BIT     1,A        ;FSW FWD ?
04A0 200B            546           JR      NZ,FSREV   ;JP IF NO
04A2 3A4000          547           LD      A,[INBUF]
04A5 CB5F            548           BIT     3,A        ;OSC MODE ?
04A7 2811            549           JR      Z,RUNMOT   ;JP IF YES
04A9 CBD7            550           SET     2,A        ;SET FWD DIR
04AB 180D            551           JR      RUNMOT
04AD CB57            552  FSREV    BIT     2,A        ;FSW REV ?
04AF 200F            553           JR      NZ,FOF     ;JP IF NO
04B1 3A4000          554           LD      A,[INBUF]
04B4 CB5F            555           BIT     3,A        ;OSC MODE ?
04B6 2802            556           JR      Z,RUNMOT   ;JP IF YES
04B8 CB97            557           RES     2,A        ;SET REV DIR
04BA CBE7            558  RUNMOT   SET     4,A        ;RUN MOT
04BC CBF7            559           SET     6,A        ;FSW ON FLG
04BE 1807            560           JR      LDINB
04C0 3A4000          561  FOF      LD      A,[INBUF]
04C3 CBA7            562           RES     4,A        ;STOP MOT
04C5 CBB7            563           RES     6,A        ;FSW FLG OFF
04C7 324000          564  LDINB    LD      [INBUF],A
04CA C9              565           RET
                     566  *
                     567  *** SUBROUTINE TO CONVERT SPEED TO DECIMAL ***
04CB DD214004        568  BNBCD    LD      IX,DISBUF
04CF FD214001        569           LD      IY,SPLB
04D3 AF              570           XOR     A          ;ZERO A REG
04D4 328000          571           LD      [8000H],A
```

```
LOCATION OBJECT CODE LINE       SOURCE LINE

04D7 326000      572        LD      [6000H],A
04DA 324060      573        LD      [4060H],A
04DD FD6E00      574        LD      L,[IY+0]        ;BIN IN HL
04E0 FD6601      575        LD      H,[IY+1]
04E3 01FC18      576        LD      BC,-1000D
04E6 CD04F9      577        CALL    DECNO           ;GET MSD
04E9 01FF9C      578        LD      BC,-100D
04EC CD04F9      579        CALL    DECNO
04EF 01FFF6      580        LD      BC,-10D
04F2 CD04F9      581        CALL    DECNO
04F5 DD7500      582        LD      [IX+0],L        ;STORE LSD
04F8 C9          583        RET
                 584 *
04F9 AF          585 DECNO  XOR     A
04FA 5D          586        LD      E,L
04FB 54          587        LD      D,H
04FC 3C          588        INC     A
04FD 09          589        ADD     HL,BC           ;SUBTRACT
04FE DA04FA      590        JP      C,(DECNO+1)
0501 6B          591        LD      L,E             ;REMAINDER IN HL
0502 62          592        LD      H,D
0503 3D          593        DEC     A
0504 F5          594        PUSH    AF
0505 2010        595        JR      NZ,NOBLK
0507 3A4060      596        LD      A,[4060H]
050A FE00        597        CP      00H
050C 2009        598        JR      NZ,NOBLK
050E F1          599        POP     AF
050F 3E0F        600        LD      A,0FH
0511 DD7700      601        LD      [IX+0],A        ;STORE BLANK
0514 DD23        602        INC     IX
0516 C9          603        RET
0517 F1          604 NOBLK  POP     AF
0518 DD7700      605        LD      [IX+0],A        ;STORE DIGIT
051B 3E01        606        LD      A,01H
051D 324060      607        LD      [4060H],A       ;FLAG
0520 DD23        608        INC     IX
0522 C9          609        RET
                 610
                 611 *** SUBROUTINE TO DISPLAY RPM ***
0523 114004      612 DISP   LD      DE,DISBUF       ;4040
0526 0E00        613        LD      C,SEG
0528 0600        614        LD      B,00H
052A 3A4000      615        LD      A,[INBUF]
052D CB6F        616        BIT     5,A             ;? JOG
052F CA0545      617        JP      Z,NUMER         ;NO,JP
0532 3E0A        618        LD      A,0AH           ; "-"
0534 ED79        619        OUT     [C],A
0536 3E1A        620        LD      A,1AH           ; "-"
0538 ED79        621        OUT     [C],A
053A 3E2A        622        LD      A,2AH           ; "-"
053C ED79        623        OUT     [C],A
053E 3E3A        624        LD      A,3AH           ; "-"
0540 ED79        625        OUT     [C],A
0542 C30551      626        JP      STEP
0545 CD0586      627 NUMER  CALL    DIGIT           ;MSD
0548 CD0586      628        CALL    DIGIT
054B CD0586      629        CALL    DIGIT
054E CD0586      630        CALL    DIGIT           ;LSD
0551 CD0590      631 STEP   CALL    SCALE           ;GRAPH SIZE
0554 CD0618      632        CALL    BARG
0557 3A4003      633        LD      A,[OUTBUF]
055A 57          634        LD      D,A
055B 3A4000      635        LD      A,[INBUF]
055E 47          636        LD      B,A
```

LOCATION OBJECT CODE  LINE      SOURCE LINE

```
055F  E683         637           AND     083H
0561  FE00         638           CP      00H         ;LO SPD ?
0563  2008         639           JR      NZ,TRES     ;NO,JP
0565  CBFA         640           SET     7,D         ;LO
0567  CBAA         641           RES     5,D
0569  CBB2         642           RES     6,D
056B  1812         643           JR      LDIT
056D  FE02         644  TRES     CP      02          ;MED SPD ?
056F  2008         645           JR      NZ,TBUR     ;NO,JP
0571  CBF2         646           SET     6,D         ;MED
0573  CBAA         647           RES     5,D
0575  CBBA         648           RES     7,D
0577  1806         649           JR      LDIT
0579  CBEA         650  TBUR     SET     5,D         ;HI
057B  CBB2         651           RES     6,D
057D  CBBA         652           RES     7,D
057F  7A           653  LDIT     LD      A,D
0580  324003       654           LD      [OUTBUF],A
0583  D360         655           OUT     [LITE],A
0585  C9           656           RET
                   657  *
0586  1A           658  DIGIT    LD      A,[DE]      ;FETCH BCD
0587  B0           659           OR      B           ;ADR MASK
0588  ED79         660           OUT     [C],A       ;WRITE
058A  13           661           INC     DE
058B  3E10         662           LD      A,10H
058D  80           663           ADD     A,B
058E  47           664           LD      B,A
058F  C9           665           RET
                   666  *
0590  3A4000       667  SCALE    LD      A,[INBUF]
0593  E683         668           AND     83H
0595  FE00         669           CP      00H         ;LO RNG ?
0597  280E         670           JR      Z,LDGLR     ;JP IF YES
0599  FE02         671           CP      02H         ;MED RNG ?
059B  2810         672           JR      Z,LDGMR     ;JP IF YES
059D  FE01         673           CP      01H         ;HI RNG ?
059F  2812         674           JR      Z,LDGHR     ;YES,JP
05A1  FD2105F8     675           LD      IY,GFR      ;* IF FULL RNG
05A5  1810         676           JR      CKOSPD
05A7  FD2105DE     677  LDGLR    LD      IY,GLR
05AB  180A         678           JR      CKOSPD
05AD  FD2105EB     679  LDGMR    LD      IY,GMR
05B1  1804         680           JR      CKOSPD
05B3  FD2105D1     681  LDGHR    LD      IY,GHR
05B7  2A4001       682  CKOSPD   LD      HL,[SPLB]   ;NEW RPM
05BA  ED5B4019     683           LD      DE,[OLDSPD] ;OLD RPM
05BE  37           684           SCF
05BF  3F           685           CCF
05C0  ED52         686           SBC     HL,DE       ;SPEED CHG ?
05C2  2808         687           JR      Z,NOCHG     ;JP IF NO
05C4  2A4001       688           LD      HL,[SPLB]
05C7  224019       689           LD      [OLDSPD],HL
05CA  FDE9         690           JP      [IY]
05CC  3A401B       691  NOCHG    LD      A,[OLDRDG]
05CF  5F           692           LD      E,A
05D0  C9           693           RET
05D1  1105DC       694  GHR      LD      DE,1500D    ;HI SPD
05D4  063B         695           LD      B,3BH       ;ENTER .020
05D6  DD21A3D7     696           LD      IX,0A3D7H
05DA  DDE5         697           PUSH    IX
05DC  1825         698           JR      GCALC
05DE  1100EB       699  GLR      LD      DE,235D     ;LO SPD
05E1  063D         700           LD      B,3DH       ;ENTER .12
05E3  DD21F837     701           LD      IX,0F837H
```

| LOCATION | OBJECT CODE | LINE | SOURCE LINE | | | |
|---|---|---|---|---|---|---|
| 05E7 | DDE5 | 702 | | PUSH | IX | |
| 05E9 | 1818 | 703 | | JR | GCALC | |
| 05EB | 1101F4 | 704 | GMR | LD | DE,500D | ;MED SPD |
| 05EE | 063D | 705 | | LD | B,3DH | ;ENTER .05 |
| 05F0 | DD216666 | 706 | | LD | IX,06666H | |
| 05F4 | DDE5 | 707 | | PUSH | IX | |
| 05F6 | 180B | 708 | | JR | GCALC | |
| 05F8 | 1100EB | 709 | GFR | LD | DE,235D | ;FULL SPD |
| 05FB | 063A | 710 | | LD | B,3AH | ;ENTER .009 |
| 05FD | DD2190B7 | 711 | | LD | IX,090B7H | |
| 0601 | DDE5 | 712 | | PUSH | IX | |
| 0603 | 37 | 713 | GCALC | SCF | | |
| 0604 | 3F | 714 | | CCF | | |
| 0605 | ED52 | 715 | | SBC | HL,DE | |
| 0607 | EB | 716 | | EX | DE,HL | |
| 0608 | CD0000 | 717 | | CALL | FLOT | ;IN C-D-E |
| 060B | E1 | 718 | | POP | HL | ;IN B-H-L |
| 060C | CD0000 | 719 | | CALL | FMPY | ;MULTIPLY |
| 060F | CD0000 | 720 | | CALL | FIXX | ;RESULT IN E |
| 0612 | 1C | 721 | | INC | E | |
| 0613 | 7B | 722 | | LD | A,E | |
| 0614 | 32401B | 723 | | LD | [OLDRDG],A | |
| 0617 | C9 | 724 | | RET | | |
| | | 725 | * | | | |
| 0618 | 3A400E | 726 | BARG | LD | A,[GRAPH+2] | |
| 061B | F5 | 727 | | PUSH | AF | |
| 061C | 21400C | 728 | | LD | HL,GRAPH | |
| 061F | 3EFF | 729 | | LD | A,0FFH | ;SEGS OFF |
| 0621 | 0603 | 730 | | LD | B,03D | ;BYTE COUNTER |
| 0623 | 77 | 731 | CBR | LD | [HL],A | |
| 0624 | 23 | 732 | | INC | HL | |
| 0625 | 05 | 733 | | DEC | B | |
| 0626 | 20FB | 734 | | JR | NZ,CBR | |
| 0628 | 21400C | 735 | | LD | HL,GRAPH | |
| 062B | 0608 | 736 | GSEG | LD | B,08H | ;BIT COUNTER |
| 062D | 1D | 737 | NXT | DEC | E | ;# SEGS ON |
| 062E | FA0639 | 738 | | JP | M,SHOW | |
| 0631 | CB26 | 739 | | SLA | [HL] | |
| 0633 | 05 | 740 | | DEC | B | |
| 0634 | 20F7 | 741 | | JR | NZ,NXT | |
| 0636 | 23 | 742 | | INC | HL | ;NEXT LOC. |
| 0637 | 18F2 | 743 | | JR | GSEG | |
| 0639 | 21400C | 744 | SHOW | LD | HL,GRAPH | |
| 063C | 7E | 745 | | LD | A,[HL] | |
| 063D | D310 | 746 | | OUT | [BAR1],A | |
| 063F | 23 | 747 | | INC | HL | |
| 0640 | 7E | 748 | | LD | A,[HL] | |
| 0641 | D320 | 749 | | OUT | [BAR2],A | |
| 0643 | 23 | 750 | | INC | HL | |
| 0644 | 7E | 751 | | LD | A,[HL] | |
| 0645 | E60F | 752 | | AND | 0FH | |
| 0647 | 47 | 753 | | LD | B,A | |
| 0648 | F1 | 754 | | POP | AF | |
| 0649 | E6F0 | 755 | | AND | 0F0H | |
| 064B | B0 | 756 | | OR | B | |
| 064C | 32400E | 757 | | LD | [GRAPH+2],A | |
| 064F | D380 | 758 | | OUT | [BAR3],A | |
| 0651 | C9 | 759 | | RET | | |
| | | 760 | | | | |
| | | 761 | *** SUBROUTINE FOR TIME DELAYS *** | | | |
| 0652 | D9 | 762 | WAIT | EXX | | |
| 0653 | 08 | 763 | | EX | AF,AF' | |
| 0654 | FDE5 | 764 | | PUSH | IY | |
| 0656 | D1 | 765 | | POP | DE | |
| 0657 | 1B | 766 | LOOP | DEC | DE | |

```
LOCATION OBJECT CODE LINE        SOURCE LINE 0658 7A           767        LD      A,D
0659 328000       768        LD      [8000H],A
065C 326000       769        LD      [6000H],A
065F B3           770        OR      E
0660 20F5         771        JR      NZ,LOOP
0662 D9           772        EXX
0663 08           773        EX      AF,AF'
0664 C9           774        RET
                  775
                  776 *** SUBROUTINE TO START MOTOR ***
0665 2A4001       777 RUN    LD      HL,[SPLB]       ;FETCH SPEED
0668 EB           778        EX      DE,HL
0669 CD0000       779        CALL    FLOT            ;IN C-D-E
066C 3A4000       780        LD      A,[INBUF]
066F E683         781        AND     83H
0671 FE80         782        CP      80H             ;FULL SPD ?
0673 2844         783        JR      Z,CFV           ;YES,JP
0675 FE01         784        CP      01H             ;HI SPD ?
0677 282C         785        JR      Z,CBV           ;YES,JP
0679 FE02         786        CP      02H             ;MED SPD ?
067B 2814         787        JR      Z,CRV           ;YES,JP
                  788 ; shaver    Y = 0.095X-1.13
067D 063D         789        LD      B,3DH           ;ENTER 0.095
067F 21C28F       790        LD      HL,0C28FH
0682 CD0000       791        CALL    FMPY
0685 CD0000       792        CALL    FIXX            ;IN DE
0688 210001       793        LD      HL,01D
068B EB           794        EX      DE,HL
068C ED52         795        SBC     HL,DE
068E 5D           796        LD      E,L             ;RESULT IN E
068F 183A         797        JR      VCAL
                  798 ; resector   Y = .095X-1.5
0691 063D         799 CRV    LD      B,3DH           ;ENTER .095
0693 21C28F       800        LD      HL,0C28FH
0696 CD0000       801        CALL    FMPY
0699 CD0000       802        CALL    FIXX            ;RESULT IN E
069C 210001       803        LD      HL,01D
069F EB           804        EX      DE,HL
06A0 ED52         805        SBC     HL,DE
06A2 5D           806        LD      E,L
06A3 1826         807        JR      VCAL
                  808 ; burr      Y = .111X-21.5
06A5 063D         809 CBV    LD      B,3DH           ;ENTER .111
06A7 21E353       810        LD      HL,0E353H
06AA CD0000       811        CALL    FMPY
06AD CD0000       812        CALL    FIXX            ;IN E
06B0 210016       813        LD      HL,22D
06B3 EB           814        EX      DE,HL
06B4 ED52         815        SBC     HL,DE
06B6 5D           816        LD      E,L
06B7 1812         817        JR      VCAL
                  818 ;FULL SPD RANGE V = .103X-1.73
06B9 063D         819 CFV    LD      B,3DH           ;ENTER .103
06BB 21D2F1       820        LD      HL,0D2F1H
06BE CD0000       821        CALL    FMPY
06C1 CD0000       822        CALL    FIXX            ;RESULT IN DE
06C4 210002       823        LD      HL,02
06C7 EB           824        EX      DE,HL
06C8 ED52         825        SBC     HL,DE
06CA 5D           826        LD      E,L
06CB 3A4000       827 VCAL   LD      A,[INBUF]
06CE CB6F         828        BIT     5,A             ;? JOG MODE
06D0 2051         829        JR      NZ,VCM          ;JP IF YES
06D2 CD073A       830        CALL    DIRCHG
06D5 CBD7         831        SET     2,A             ;SET RUN
```

```
LOCATION OBJECT CODE  LINE         SOURCE LINE

06D7 324003           832          LD      [OUTBUF],A
06DA D360             833          OUT     [LITE],A        ;MOTOR ON
06DC 7B               834          LD      A,E
06DD D330             835          OUT     [DAC],A         ;VELOCITY
06DF 3A4000           836          LD      A,[INBUF]
06E2 32401C           837          LD      [OLDINB],A
06E5 CB5F             838          BIT     3,A             ;?OSC
06E7 2809             839          JR      Z,OSC           ;YES,JP
06E9 3A400F           840          LD      A,[FLAGS]
06EC CB97             841          RES     2,A
06EE 32400F           842          LD      [FLAGS],A
06F1 C9               843          RET
06F2 3A400F           844 OSC      LD      A,[FLAGS]
06F5 CB57             845          BIT     2,A             ;OSC TIMER ACTV ?
06F7 200B             846          JR      NZ,OSCTIM
06F9 CBD7             847          SET     2,A
06FB 32400F           848          LD      [FLAGS],A
06FE 210055           849          LD      HL,0055H
0701 224014           850          LD      [CTR3],HL
0704 ED5B4014         851 OSCTIM   LD      DE,[CTR3]       ;GET COUNT
0708 1B               852          DEC     DE
0709 7A               853          LD      A,D
070A B3               854          OR      E
070B 2011             855          JR      NZ,STDAT3
070D 3A4000           856          LD      A,[INBUF]
0710 EE04             857          XOR     04H             ;FLIP FWD/REV
0712 324000           858          LD      [INBUF],A
0715 3A400F           859          LD      A,[FLAGS]
0718 CB97             860          RES     2,A
071A 32400F           861          LD      [FLAGS],A
071D C9               862          RET
071E ED534014         863 STDAT3   LD      [CTR3],DE       ;SAVE COUNT
0722 C9               864          RET
0723 3A4000           865 VCM      LD      A,[INBUF]       ;* IF JOG MODE
0726 CB67             866          BIT     4,A             ;? RUN
0728 C8               867          RET     Z
0729 3E01             868          LD      A,01H
072B D330             869          OUT     [DAC],A
072D 3A4003           870          LD      A,[OUTBUF]
0730 CBD7             871          SET     2,A             ;MOT START BIT
0732 CBCF             872          SET     1,A             ;SET FWD LITE
0734 324003           873          LD      [OUTBUF],A
0737 D360             874          OUT     [LITE],A        ;START
0739 C9               875          RET
                      876 *
073A FD2103FF         877 DIRCHG   LD      IY,03FFH
073E 214000           878          LD      HL,INBUF
0741 3A401C           879          LD      A,[OLDINB]
0744 47               880          LD      B,A
0745 3A4003           881          LD      A,[OUTBUF]
0748 CB56             882          BIT     2,[HL]          ;REV THIS TIME ?
074A 280F             883          JR      Z,REVDIR        ;JP IF YES
074C CB50             884          BIT     2,B             ;FWD LAST TIME ?
074E 2022             885          JR      NZ,SET1         ;JP IF YES
0750 CB97             886          RES     2,A             ;MOTOR OFF
0752 D360             887          OUT     [LITE],A
0754 CD0652           888          CALL    WAIT
0757 CBCF             889          SET     1,A             ;SET FWD
0759 180D             890          JR      DEL2
075B CB50             891 REVDIR   BIT     2,B             ;REV LST TIME ?
075D 2816             892          JR      Z,RES1          ;JP IF YES
075F CB97             893          RES     2,A             ;MOTOR OFF
0761 D360             894          OUT     [LITE],A
0763 CD0652           895          CALL    WAIT
0766 CB8F             896          RES     1,A             ;SET REV
```

```
LOCATION OBJECT CODE LINE       SOURCE LINE

0768 D360        897 DEL2    OUT     [LITE],A
076A FD210010    898         LD      IY,0010H
076E CD0652      899         CALL    WAIT
0771 C9          900         RET
0772 CBCF        901 SET1    SET     1,A             ;FWD DIR
0774 C9          902         RET
0775 CB8F        903 RES1    RES     1,A             ;REV DIR
0777 C9          904         RET
                 905 *
                 906 *** SUBROUTINE TO TEST LITES AND DIGITS ***
0778 328000      907 CHECK   LD      [8000H],A
077B 326000      908         LD      [6000H],A
077E 3E0C        909         LD      A,0CH
0780 324000      910         LD      [INBUF],A
0783 3EEB        911         LD      A,235D
0785 324001      912         LD      [SPLB],A
0788 AF          913         XOR     A
0789 324002      914         LD      [SPHB],A
078C 3E08        915         LD      A,08H
078E D360        916         OUT     [LITE],A
0790 3E2F        917         LD      A,02FH
0792 32400E      918         LD      [GRAPH+2],A
0795 D380        919         OUT     [BAR3],A
0797 3E0F        920         LD      A,0FH
0799 CD087A      921         CALL    DIGOUT
079C 114004      922         LD      DE,DISBUF
079F CD015C      923         CALL    DIGITS
07A2 1E00        924         LD      E,00H
07A4 CD0618      925         CALL    BARG
07A7 CD0867      926         CALL    DELAY
07AA 3E06        927         LD      A,REVLEV
07AC 324007      928         LD      [DISBUF+3],A
07AF CD087D      929         CALL    (DIGOUT+3)
07B2 CD0867      930         CALL    DELAY
07B5 CD0867      931         CALL    DELAY
07B8 CD0867      932         CALL    DELAY
07BB CD0867      933         CALL    DELAY
07BE 3E08        934         LD      A,08H
07C0 CD087A      935         CALL    DIGOUT
07C3 CD0867      936         CALL    DELAY
07C6 3E0F        937         LD      A,0FH           ;BLANKS TO DISPLAY
07C8 CD087A      938         CALL    DIGOUT
07CB 3E08        939         LD      A,08H           ;8'S TO DSPLY BUF
07CD CD086F      940         CALL    FILBUF
07D0 0E90        941         LD      C,SEG2          ;8'S IN RPM LO
07D2 0640        942         LD      B,40H
07D4 210004      943         LD      HL,04H
07D7 114004      944         LD      DE,DISBUF
07DA CD0163      945         CALL    NXTDIG
07DD CD0867      946         CALL    DELAY
07E0 3E0F        947         LD      A,0FH           ;BLANK RPM LO
07E2 CD086F      948         CALL    FILBUF
07E5 0E90        949         LD      C,SEG2
07E7 0640        950         LD      B,040H
07E9 210004      951         LD      HL,04H
07EC 114004      952         LD      DE,DISBUF
07EF CD0163      953         CALL    NXTDIG
07F2 1E14        954         LD      E,20D           ;DSPLY BAR GRAPH
07F4 CD0618      955         CALL    BARG
07F7 CD0867      956         CALL    DELAY
07FA 1E00        957         LD      E,00H
07FC CD0618      958         CALL    BARG
07FF 3E08        959         LD      A,08H           ;8'S TO DSPLY BUF
0801 CD086F      960         CALL    FILBUF
0804 0E90        961         LD      C,SEG2          ,8'S TO RPM HI
```

LOCATION OBJECT CODE LINE      SOURCE LINE

```
0806 0600           962            LD      B,00H
0808 210004         963            LD      HL,04H
080B 114004         964            LD      DE,DISBUF
080E CD0163         965            CALL    NXTDIG
0811 CD0867         966            CALL    DELAY
0814 3E0F           967            LD      A,0FH           ;BLANK DSPLY BUF
0816 CD086F         968            CALL    FILBUF
0819 0E90           969            LD      C,SEG2
081B 0600           970            LD      B,00H
081D 210004         971            LD      HL,04H
0820 114004         972            LD      DE,DISBUF
0823 CD0163         973            CALL    NXTDIG
0826 3E88           974            LD      A,88H           ;DSPLY LO
0828 D360           975            OUT     [LITE],A
082A CD0867         976            CALL    DELAY
082D 3E48           977            LD      A,48H           ;DSPLY MED
082F D360           978            OUT     [LITE],A
0831 CD0867         979            CALL    DELAY
0834 3E28           980            LD      A,28H           ;DSPLY HI
0836 D360           981            OUT     [LITE],A
0838 CD0867         982            CALL    DELAY
083B 3E0A           983            LD      A,0AH           ;DSPLY FWD
083D D360           984            OUT     [LITE],A
083F CD0867         985            CALL    DELAY
0842 3E1A           986            LD      A,1AH           ;DSPLY FTSW
0844 D360           987            OUT     [LITE],A
0846 CD0867         988            CALL    DELAY
0849 3E1F           989            LD      A,01FH
084B D380           990            OUT     [BAR3],A        ;DSPLY NORM & CONT
084D CD0867         991            CALL    DELAY
0850 3E02           992            LD      A,02H
0852 D360           993            OUT     [LITE],A        ;AUDIO ON
0854 CD0867         994            CALL    DELAY
0857 3E0A           995            LD      A,0AH           ;AUDIO OFF
0859 D360           996            OUT     [LITE],A
085B 110891         997            LD      DE,LORNG
085E CD015C         998            CALL    DIGITS
0861 3E8A           999            LD      A,08AH
0863 324003         1000           LD      [OUTBUF],A
0866 C9             1001           RET
                    1002   *
0867 FD217FFF       1003   DELAY   LD      IY,07FFFH
086B CD0652         1004           CALL    WAIT
086E C9             1005           RET
                    1006   *
086F 214004         1007   FILBUF  LD      HL,DISBUF
0872 0609           1008           LD      B,09D
0874 05             1009   SEV     DEC     B
0875 C8             1010           RET     Z
0876 77             1011           LD      [HL],A
0877 23             1012           INC     HL
0878 18FA           1013           JR      SEV
                    1014   *
087A CD086F         1015   DIGOUT  CALL    FILBUF
087D 114004         1016           LD      DE,DISBUF
0880 0E00           1017           LD      C,SEG
0882 0600           1018           LD      B,00H
0884 CD0586         1019           CALL    DIGIT
0887 CD0586         1020           CALL    DIGIT
088A CD0586         1021           CALL    DIGIT
088D CD0586         1022           CALL    DIGIT
0890 C9             1023           RET
                    1024   *
                    1025   *DATA CONSTANTS
                    1026   *
```

```
LOCATION OBJECT CODE LINE      SOURCE LINE 0891 0F            1027 LORNG   DEFB    0FH
 0892 04            1028         DEFB    04H
 0893 00            1029         DEFB    00H
 0894 00            1030         DEFB    00H
 0895 05            1031         DEFB    05H
 0896 03            1032         DEFB    03H
 0897 02            1033         DEFB    02H
 0898 0F            1034         .DEFB   0FH
 0899 0F            1035 MIDRNG  DEFB    0FH
 089A 09            1036         DEFB    09H
 089B 00            1037         DEFB    00H
 089C 00            1038         DEFB    00H
 089D 00            1039         DEFB    00H
 089E 00            1040         DEFB    00H
 089F 05            1041         DEFB    05H
 08A0 0F            1042         DEFB    0FH
 08A1 02            1043 HIRNG   DEFB    02H
 08A2 05            1044         DEFB    05H
 08A3 00            1045         DEFB    00H
 08A4 00            1046         DEFB    00H
 08A5 00            1047         DEFB    00H
 08A6 00            1048         DEFB    00H
 08A7 05            1049         DEFB    05H
 08A8 01            1050         DEFB    01H
 08A9 02            1051 FULRNG  DEFB    02H
 08AA 05            1052         DEFB    05H
 08AB 00            1053         DEFB    00H
 08AC 00            1054         DEFB    00H
 08AD 05            1055         DEFB    05H
 08AE 03            1056         DEFB    03H
 08AF 02            1057         DEFB    02H
 08B0 0F            1058         DEFB    0FH
                    1059 *
                    1060 *DEFINED STORAGE AREAS
                    1061 *
                    1062         ORG     4000H
 4000               1063 INBUF   DEFS    1D
 4001               1064 SPLB    DEFS    1D
 4002               1065 SPHB    DEFS    1D
 4003               1066 OUTBUF  DEFS    1D
 4004               1067 DISBUF  DEFS    8D
 400C               1068 GRAPH   DEFS    3D
 400F               1069 FLAGS.  DEFS    1D
 4010               1070 CTR1    DEFS    2D
 4012               1071 CTR2    DEFS    2D
 4014               1072 CTR3    DEFS    2D
 4016               1073 CTR4    DEFS    1D
 4017               1074 CTR5    DEFS    2D
 4019               1075 OLDSPD  DEFS    2D
 401B               1076 OLDRDG  DEFS    1D
 401C               1077 OLDINB  DEFS    1D

Errors=   0
```

What is claimed is:

1. A disposable, single use cutting blade assembly for use with a handpiece having motor means for rotatably driving said cutting blade assembly, bore means for receiving said cutting blade assembly and sensing means disposed adjacent said bore means, said cutting blade assembly comprising an elongate tubular outer member having a distal end with an opening therein and a proximal end;

an elongate inner member received in said outer member and having a distal cutting end disposed adjacent said opening in said distal end of said outer member and a proximal end adapted to be received in the bore means of the handpiece and rotatably driven by the motor means to rotate in said outer member; and a plastic hub mounted on said proximal end of said outer member and having a configuration to be received in the bore means of the handpiece in a particular orientation relative to the sensing means, said plastic hub including first and second annular sections, at least one of said first and second annular sections having recess means therein, coding means disposed in said recess means having a characteristic detectable by said sensing means, said first and second annular sections being secured together to close said recess means and hold said coding means in said recess means whereby said cutting blade assembly can be identified by the sensing means in the handpiece detecting the presence of said coding means.

2. A disposable, single use cutting blade assembly according to claim 1 wherein said coding means includes at least one magnet.

3. A disposable, single use cutting blade assembly according to claim 1 wherein said recess means includes a plurality of spaced recesses and said coding means includes at least one magnet disposed in at least one of said recesses.

4. A disposable, single use cutting blade assembly according to claim 3 wherein said first and second annular sections are welded together.

* * * * *

UNITED STATES PATENT AND TRADEMARK OFFICE
CERTIFICATE OF CORRECTION

PATENT NO. : 5,269,794

DATED : December 14, 1993

INVENTOR(S) : Fred Rexroth

It is certified that error appears in the above-identified patent and that said Letters Patent is hereby corrected as shown below:

Column 1, lines 56 - 57, delete "Dynoics" and replace with --Dyonics--.

Column 2, line 6, delete "comprising" and replace with --compromising--.

Column 8, line 41, delete "tan" and replace with --tang--.

Column 8, line 62, delete "automatically" and replace with --ultrasonically--.

Column 9, line 66, delete "read" and replace with --reed--.

Column 11, lines 28 - 29, delete "It is to be noted that slots and with slot 103 in bore section 50.".

UNITED STATES PATENT AND TRADEMARK OFFICE
CERTIFICATE OF CORRECTION

PATENT NO. : 5,269,794

DATED : December 14, 1993

INVENTOR(S) : Fred Rexroth

It is certified that error appears in the above-identified patent and that said Letters Patent is hereby corrected as shown below:

Column 12, line 8, delete "are" and replace with --that--.

Column 12, line 45, delete "where" and replace with --here--.

Column 12, line 59, after "TEFLON" insert --(polytetrafluorethylene)--.

Column 13, line 65, delete "location" and insert --locations--.

Column 15, line 11, delete "and" (first occurrence) and replace with --through--.

Column 18, lines 51 - 52, delete "components" and replace with --component--.

Signed and Sealed this

Eighteenth Day of October, 1994

Attest:

BRUCE LEHMAN

Attesting Officer

Commissioner of Patents and Trademarks